(12) United States Patent
Graner et al.

(10) Patent No.: US 6,875,849 B2
(45) Date of Patent: Apr. 5, 2005

(54) METHODS OF RECOVERING CHAPERONE PROTEINS AND COMPLEXES THEREOF

(75) Inventors: Michael Graner, Tucson, AZ (US); Emmanuel Katsanis, Tucson, AZ (US)

(73) Assignee: Arizona Board of Regents of behalf of The University of Arizona, Tucson, AZ (US)

( * ) Notice: Subject to any disclaimer, the term of this patent is extended or adjusted under 35 U.S.C. 154(b) by 158 days.

(21) Appl. No.: 10/091,390

(22) Filed: Mar. 5, 2002

(65) Prior Publication Data

US 2003/0031661 A1 Feb. 13, 2003

Related U.S. Application Data

(60) Provisional application No. 60/287,967, filed on May 1, 2001.

(51) Int. Cl.$^7$ ............................. C07K 1/14; C07K 1/00; A61K 38/00; C25B 7/00
(52) U.S. Cl. .......................... 530/412; 530/350; 514/2; 204/459
(58) Field of Search ................................. 530/350, 412, 530/427; 204/459; 514/2

(56) References Cited

U.S. PATENT DOCUMENTS

| | | | | |
|---|---|---|---|---|
| 4,588,492 A | * | 5/1986 | Bier ........................... | 204/629 |
| 5,298,143 A | * | 3/1994 | Ivory et al. .................. | 204/543 |
| 5,750,119 A | | 5/1998 | Srivastava | |
| 5,837,251 A | | 11/1998 | Srivastava | |
| 5,935,576 A | | 8/1999 | Srivastava | |
| 5,961,979 A | | 10/1999 | Srivastava | |
| 5,997,873 A | | 12/1999 | Srivastava | |

OTHER PUBLICATIONS

Osuji et al. "Pesticide Inactivation of Peanut Glutamate Dehydrogenase: Biochemical Basis of the Enzyme's Isomerization" (1999) J. Agric. Food Chem., 47(8), 3345–3351.*
Shang et al., "Carrier Ampholyte–Free Solution Isoelectric Focusing as a Prefractionation Method for the Proteomic Analysis of Complex Protein Mixtures" (2003) Electrophoresis, 14(14), 2359–2368.*
Nieves et al. "Covalent Modifications of Membrane Proteins with Unanticipated Acid Shifts in Isoelectric Points" (1998) ABRF 98 Poster Session, Mar. 22–24, 1998, Program #87.*
Rotofor System Bio–Rad Tech Note Summaries.*
Blennow et al., "Isolation and Biochemical Characterization of Highly Purified *Escherichia coli* Molecular Chaperone C[n60 (GroRL) by Affinity Chromatography and Urea–Induced Monomerization" (1995) Biochim. Biophys. Acta, 1252(1), 69–78.*
Eriksson et al., "The Superantigenic Activity of Streptococcal Pyrogenic Exotoxin B is Independent of the Protease Activity" (1999) FEMS Immunol. Med. Microbiol., 25(4), 355–363.*

Large et al., "Properties of the Chaperonin Complex from the Halophilic Archaeon Halofrax volcanii" (2002) FEBS Lett., 532(3), 309–312.*
Quait–Randall et al., "Purification of Chaperonins" (1999) J. Chromatog. B, 722(1–2), 153–177.*
Atkins et al., "Overproduction And Purification Of Mycobacterium Tuberculosis Chaperonin–10; Autographa Californica Nuclear–Polyhedrosis Virus Vector Acrp6.sC Expression in Spodoptera frugiperda Insect Cell Culture" (1994) Gene, vol. 150, No. 1, pp. 145–148.*
Zeng e al., "Tumor–Derived, Chaperone–Rich Cell Lysate Activates Dendritic Cells and Elicits Potent Antitumor Activity" (2003) Blood, 101(11), 4485–4491.*
Joachimiak et al., (Purification of Chaperonins from Thermophilic Bacteria and Archaea (1997) J. Chromatog. A, 773(1–2), 131–138.*
Salvucci et al., "Heat Shock Proteins in Whiteflies, an Insect that Accumulates Sorbitol in Response to Heat Stress" (2000) J. Thermal Biol., 25(5), 363–371.*
Minto et al., "Mycobacterial Cpn10 Promotes Recognition of the Mammalian Homologue by a Mycobacterium–Specific Antiserum" (Jun. 22, 1998) Biochim. Biophys. Acta, vol. 1403, No. 2, pp. 151–157.*
Lucietto et al., "Mycobacterium tuberculosis Chaperonin 10 and N–Truncated Fragments—Their Synthesis and Purification by the Isoelectric Focusing Technique Carried out in Solution" (Apr. 1997) J. Peptide Res., vol. 49, No. 4, pp. 308–323.*
Jethmalani et al., "Partial homology of Stress Glycoprotein GP62 with HSP70"(Apr. 10, 1997) Exp. Cell Res., vol. 232, No. 1, pp. 8–16.*
Mol et al., "*Escherichia–Coli* Periplasmic Chaperone Faee is a Homodimer and the Chaperone–K88 Subunit Complex is a Heterotrimer" (Jan. 1994) Molec. Microbiol., vol. 11, No. 2, pp. 391–402.*
Amato et al., 1999, "Active Specific Immunotherapy in Patients with Renal Cell Carcinoma (RCC) Using Autologous Tumor Derived Heat Shock Protein–Peptide Complex–96 (HSPP–96) Vaccine" American Society Clinical Oncology Meeting, abstract 1278.
Arnold et al., 1995, "Cross–priming of minor histocompatibility antigen–specific cytotoxic T cells upon immunization with the heat shock protein gp96" *J. Exp. Med.* 182:885.

(Continued)

*Primary Examiner*—Jean C. Witz
*Assistant Examiner*—Susan Hanley
(74) *Attorney, Agent, or Firm*—Jones Day

(57) ABSTRACT

The present invention provides methods for efficient and concomitant recovery of multiple chaperone proteins and/or chaperone protein complexes from a limited sample source. Disclosed are methods involving the use of Free Solution Iso-Electric Focusing (FS-IEF) which can enrich samples containing chaperone proteins and/or chaperone protein complexes from a given sample. The chaperone proteins can be, but are not restricted to calreticulin, gp96, hsp86, hsp84, hsp70, hsp60 and hsp40. The invention also provides methods of recovering chaperone protein complexes for the preparation of vaccines containing chaperone complexes.

26 Claims, 5 Drawing Sheets

OTHER PUBLICATIONS

Figure 1A:
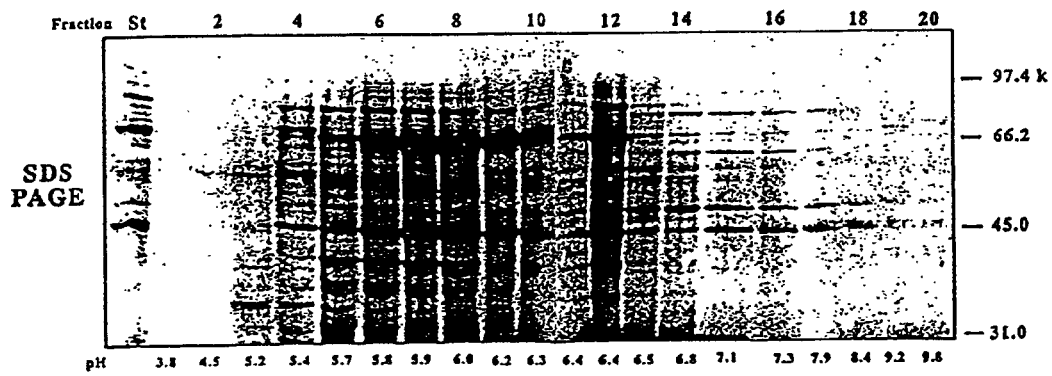

Basu and Srivastava, 1999, "Calreticulin, a peptide–binding chaperone of the endoplasmic reticulum, elicits tumor– and peptide–specific immunity" *J. Exp. Med.* 189:797.

Ciupitu et al., 1998, "Immunization with a lymphocytic choriomeningitis virus peptide mixed with heat shock protein 70 results in protective antiviral immunity and specific cytotoxic T lymphocytes" *J. Exp. Med* 5: 685.

Graner et al., 2000, "Tumor–derived multiple chaperone enrichment by free–solution isoelectric focusing yields potent antitumor vaccines" *Cancer Immunol. Immunother.* 49:476.

Graner et al. 2000, "Immunprotective activities of multiple chaperone proteins isolated from murine B–cell leukemia/lymphoma" *Clin. Can. Res.* 6:909.

Janetzki et al., 2000, "Immunization of cancer patients with autologous cancer–derived heat shock protein gp96 preparations: a pilot study" *Int. J. of Cancer* 88:232.

Ishii et al., 1999, "Isolation of MHC class I–restricted tumor antigen peptide and its precursors associated with heat shock proteins hsp70, hsp90, and gp96" *J. Immunol.* 162:1303.

Katsanis et al., 2000, "Augmentation of Tumor Lysate Immunogencity by enrichment of Chaperone Proteins Using Free Solution Isoelectric Focusing (FS–IEF)" *Keystone Symposia on Cellular Immunity and Immunotherapy of Cancer,* abstract 431.

Lewis et al., 1999, "Pilot Trial of Vaccination wwih Autologous Tumor–Derived gp96 Heat Shock Protein–Peptide Complex (HSPPC–96) in Patients with Resected Pancreatic Adenocarcinoma" *American Society Clinical Oncology Meeting,* abstract 1687.

Ménoret and Chandawarkar, 1998, "Heat–shock protein–based anticancer immunotherapy: an idea whose time has come" *Semin. in Oncology* 25:654.

Nair et al., 1999, "Careticulin displays in vivo peptide–binding activity and can elicit CTL responses against bound peptide" *Immunol.* 162:6426.

Nieland et al., 1996, "Isolation of an immunodominant viral peptide that is endogenously bound to the stress protein GP96/GRP94" *PNAS* 93:6135.

Peng et al., 1997, "Purification of immunogenic heat shock protein 70–protein 70–peptide complexes by ADP–affinity chromatogrpahy" *J. Immunol. Meth.* 204:13.

Srivatava et al., 1986, "Tumor rejection antigens of chemically induced sarcomas of inbred mice" P.N.A.S. 83:3407.

Srivastava et al., 1988, "Chromosomal assignment of the gene encoding the mouse tumor rejection antigen gp9" *Immunogenetics* 28:205.

Srivastava et al., 1991, "Stress–induced proteins in immune response to cancer" *Curr. Top. Microbiol. Immunol.* 167:109.

Srivastava, 1993, "Peptide–binding heat shock proteins in the endoplasmic reticulum: role in immune response to cancer and in antigen presentation" *Adv. Cancer Res.* 62:153.

Srivastava and Udono, 1994, "Heat shock protein–peptide complexes in cancer immunotherapy" *Curr. Opin. Immunol.* 6:728.

Srivastava et al., 1998, "Heat shock proteins come of age: primitive functions acquire new roles in an adaptive world" *Immunity* 8:657.

Tamura et al., 1997, "Immunotherapy of tumors with autologous tumor–derived heat shock protein preparations" *Science* 278:117.

Yedavelli et al., 1999, "Preventive and therapeutic effect of tumor derived heat shock protein, gp96, in an experimental prostate cancer model" *Int. J. Mol. Med.* 3:243.

Ullrich et al., 1986, "A mouse tumor–specific transplantation antigen is a heat shock–related protein" *PNAS* 83:3121.

* cited by examiner

METHODS OF RECOVERING CHAPERONE PROTEINS AND COMPLEXES THEREOF

This application claims benefit of Provisional Application No. 60/287,967 filed May 1, 2001, which is incorporated by reference herein in its entirety.

1. FIELD OF THE INVENTION

The invention relates generally to the field of vaccine development. More particularly, the present invention relates to a method of recovering chaperone proteins or chaperone protein complexes from a limited sample. A mixture of different chaperone proteins complexed with proteins or peptides can be discretely recovered from a sample by a one-step method employing free solution/isoelectric focusing (FS-IEF).

2. BACKGROUND OF THE INVENTION

In modern medicine, immunotherapy or vaccination has virtually eradicated diseases such as polio, tetanus, tuberculosis, chicken pox, measles, hepatitis, etc. The approach using vaccinations has exploited the ability of the immune system to prevent infectious diseases. Vaccination with non-live materials such as proteins generally leads to an antibody response or $CD4^+$ helper T cell response. (Raychaudhuri and Morrow (1993) *Immunology Today* 14:344). On the other hand, vaccination or infection with live materials such as live cells or infectious viruses generally leads to a $CD8^+$ cytotoxic T-lymphocyte (CTL) response. A CTL response is crucial for protection against cancers, infectious viruses and certain bacteria. This poses a practical problem, for, the only way to achieve a CTL response is to use live agents which are themselves pathogenic. The problem is generally circumvented by using attenuated viral and bacterial strains or by killing whole cells which can be used for vaccination. These strategies have worked well but the use of attenuated strains always carries the risk that the attenuated agent may recombine genetically with host DNA and turn into a virulent strain. Thus, there is need for methods which can lead to $CD8^+$ CTL response by vaccination with non-live materials such as proteins in a specific manner. It has been discovered that heat shock protein complexes have particular utility as vaccines against cancers and infectious diseases. (Srivastava et al., (1994) *Curr. Op. Immu.* 6:728; Srivastava (1993) *Adv. Cancer Res.* 62:153).

Chaperone proteins are involved in a wide array of events involving the processing and functioning of cellular proteins. Chaperone proteins were originally recognized for their protective role during cell stress. It is now clear that chaperone proteins also are involved in folding, unfolding, refolding, stabilizing, oligomerizing, salvaging, and discarding cellular proteins during the routine events of intracellular activities. Chaperone proteins perform these functions as multi-protein complexes consisting of chaperones, co-chaperones, and substrate molecules.

Heat shock proteins (HSPs) are proteins synthesized by a cell in response to heat shock. There are also some HSPs that are homologous to stress induced proteins and are expressed constitutively. HSPs can include a protein that (i) increases in concentration when a cell is exposed to a stressful stimulus; (ii) binds other proteins or peptides; and (iii) is capable of releasing the bound proteins or peptides in the presence of adenosine triphosphate (ATP) or low pH. An HSP can also be any protein or conserved homolog thereof whose intracellular concentration does not increase when a cell is exposed to stressful stimulus and that shows at least 35% homology with a known HSP protein as determined by the BLAST p algorithm. HSPs are a type of chaperone protein. Heat shock proteins fall into families such as but not limited to the families HSP25/HSP27, HSP60, HSP70 and HSP90 where the numbers reflect the approximate molecular weight of the stress proteins in kilodaltons. Heat shock proteins are capable of binding proteins or peptides, with which they form complexes endogenously in cells or in vitro under the appropriate conditions (Nair et al. (1999) *J. Immun.* 162:6426; Flynn et al. (1989) *Science* 245:385; Blachere et al. (1997) *J. Exp. Med.* 186:1315).

Immunization of mice with the gp96 complex or hsp84/86 complex isolated from a particular tumor rendered the mice immune to that particular tumor, but not to antigenically distinct tumors. Isolation and characterization of genes encoding gp96 and hsp84/86 revealed significant homology between them, and showed that gp96 and hsp84/86 were, respectively, the endoplasmic reticular and cytosolic counterparts of the same heat shock proteins (Srivastava, et al. (1988) *Immunogenetics* 28:205; Srivastava, et al. (1991) *Curr. Top. Microbiol. Immunol* 167:109). Further, hsp70 complex was shown to elicit immunity to the tumor from which it was isolated but not to antigenically distinct tumors. However, hsp70 complex depleted of peptides was found to lose its immunogenic activity (Udono and Srivastava (1993) *J. Exp. Med.* 178:1391). The observations revealed that the heat shock proteins are not immunogenic per se, but are carriers of antigenic peptides that elicit specific immunity to cancers (Srivastava (1993) *Adv. Cancer Res.* 62:153).

This phenomenon has been observed in both tumor and viral models with known and unknown antigens (Srivastava, et al. (1998) *Immunity* 8:657; Ciupitu, et al. (1998) *J. Exp. Med* 5: 685; Arnold et al. (1995) *J. Exp. Med.* 182:885). The presence of an antigenic peptide bound to gp96, hsc70, and hsp84/hsp86 has been structurally demonstrated in cells for which the antigenic peptide is known (Nieland, et al. (1996) *Proc. Nat'l. Acad. Sci. USA* 93:6135; Breloer, et al. (1998) *Eur. J. Immunol.* 28:1016; Ishii et al. (1999) *J. Immunol.* 162:1303). Vaccination with heat shock protein complexes is applicable for both the prophylactic (Srivastava, et al. (1986) *Proc. Nat'l. Acad. Sci. USA* 83:3407; Ullrich, et al. (1986) *Proc. Nat'l. Acad. Sci. USA* 83:3121; Peng, et al. (1997) *J. I. Meth.* 204:13; Basu and Srivastava (1999) *J. Exp. Med.* 189:797) and therapeutic treatment of cancer (Tamura et al. (1997) *Science* 278:117; Yedavelli, et al. (1999) *Int. J. Mol. Med* 3:243) and for the treatment of infectious diseases (Ciupitu et al. (1998) *J. Exp. Med.* 5:685). The translation of this approach to immunotherapy of human cancer is currently under investigation using either gp96 complex (Janetzki, et al.(2000) *Int. J. of Cancer* 88:232; Amato, et al. (1999) *ASCO meeting*, abstract 1278; Lewis, et al. (1999) *ASCO meeting* abstract 1687) or hsp70 complex as an autologous vaccine and the individual patient's cancers as a source of the heat shock proteins (Ménoret and Chandawarkar (1998) *Semin. in Oncology* 25:654).

The preparation and use of a customized, autologous vaccine against the tumors of individual patients is now feasible using tumor-derived hsp complexes (Ménoret and Chandawarkar (1998) *Semin. in Oncol.* 25:654). Preliminary clinical trials with this approach have demonstrated that patients immunized with gp96 complex, purified from their own tumors, develop cancer-specific $CD8^+$ T cell response (Janetzki, et al.(2000) *Int. J. of Cancer* 88:232; Lewis, et al. (1999) *ASCO meeting* abstract 1687; Amato, et al. (1999) *ASCO meeting* abstract 1278). Clinical trials using purified preparations of autologous tumor-derived hsp70 complex are being conducted for the treatment of breast carcinoma and chronic low grade leukemia. Preliminary evidence of clinical responses to purified gp96 complex has also been obtained in a trial with patients with renal carcinoma (Amato, et al. (1999) *ASCO meeting* abstract 1278). These trials rely on a time-tested immunologic principle that anti-tumor immunity is generally private (Srivastava, et al. (1998) *Immunity* 8:657; Berd, et al. (1999) *Semin. Oncol.* 25:1315), justifying the use of a patient's own tumor as the source of the anti-tumor vaccine.

Previous methods for purification of the immunogenic chaperone protein complexes led to the isolation of chaperone protein species (U.S. Pat. Nos. 5,997,873; 5,935,576; 5,750,119; 5,961,979; 5,837,251). These methods neglected the rest of the sample that could be used as a complementary source of chaperone protein-based vaccine. Therefore, it is an object of the invention to provide a method for collecting multiple chaperone proteins and chaperone protein complexes from a limited sample source.

Citation or identification of any reference herein shall not be construed as an admission that such reference is available as prior art to the present invention.

3. SUMMARY OF THE INVENTION

The present invention provides methods for enrichment and/or purification of chaperone proteins and chaperone protein complexes which are based on isoelectric focusing. The present invention also-provides compositions consisting of chaperone proteins and chaperone protein complexes which have been purified or enriched using isoelectric focusing. Methods for treating and preventing cancer and infectious diseases using enriched chaperone proteins prepared by the methods of isoelectric focusing are also provided.

In one embodiment, the methods of the invention can be used to recover or enrich one or more chaperone proteins and/or chaperone protein complexes from a sample by a method comprising placing the samples in a pH gradient, in the presence of an electric field, and collecting fractions of chaperone proteins from the gradient. Preferably, the technique of free solution isoelectric focusing (FS-IEF) is used to enrich chaperone proteins such as, caireticulin (CRT), hsp90, gp96, grp75/mt, hsp 72, hsp 60, and hsp70. FS-IEF is preferably conducted within a power range of 10–20 Watts. In one embodiment FS-IEF is performed in the presence of urea and detergent. In another embodiment FS-IEF is performed by applying a sample to a matrix comprised of a non-ionic or zwitterionic detergent and urea in the range of 4M–8M. Said matrix can also be comprised of charged particles e.g. ampholytes or Rotolytes®. In a particular embodiment the detergent is a combination of octylphenol ethylene oxide condensate (Triton X-100), octylphenoxypoly (ethyleneoxy) ethanol (Triton X-114), and tert-octylphenoxy poly(oxyethylene)ethanol (Igepal CA-630). In a further embodiment the detergent is 0.1% octylohenol ethylene oxide condensate, 0.1% octylphenoxypoly (ethyleneoxy) ethanol, and 0.1% tert-octylphenoxy poly(oxyethylene)ethanol. In another embodiment the matrix comprises salt e.g. sodium chloride.

In a particular embodiment the sample containing the chaperone proteins or chaperone protein is a cell lysate. The cell lysate can be prepared by mechanical means, or by contacting the cells with a hypertonic buffer, a hypotonic buffer, or a detergent. The sample can also be comprised of a solution containing a plurality of proteins including, but not limited to chaperone proteins or chaperone protein complexes.

In another embodiment, the methods of the invention can be used for preparing a vaccine composition, comprising the steps of placing a sample comprising antigenic chaperone protein complexes in a pH gradient, in an appropriate matrix or substrate, applying an electric current to the matrix or substrate, and collecting the enriched antigenic chaperone protein complexes from the gradient under the appropriate conditions. The enriched chaperone protein complexes can be used to make vaccine compositions for administration to a subject in need of treatment or prevention of a disease. Depending on the disease, the sample comprising antigenic chaperone protein complexes can be a lysate of cancer tissues, tumor cells, infected cells from biopsies, or transformed or transfected cells from cell cultures. However, in instances where the chaperone protein complexes are for autologous use, the source of antigenic chaperone protein complexes may not be available in large quantity, thus the methods of the invention are particularly efficient for recovering the majority of these protein complexes from a limited amount of sample.

In another embodiment, the FS-IEF methods of the invention can also be combined with other processes known in the art to further purify the individual species of chaperone and chaperone protein complexes. The methods of the invention can serve to enrich for the desired species prior to the purification process. The invention also encompasses aggregated forms of chaperone proteins and chaperone protein complexes which are observed to be present in the IEF fractions and have an estimated molecular weight of greater than 300 KD. In another embodiment the invention comprises non-covalent complexes of chaperone proteins and different peptides.

In a preferred embodiment the invention includes cytoplasmic chaperone proteins and or chaperone protein complexes that are enriched for, but not purified to homogeneity, by IEF and are present in fractions collected from IEF having a pH in the range of 4–7. The fractions can be pooled. The pooled fractions can be dialyzed. Preferably the chaperone protein complexes have a molecular weight of 300–500 kD. Most preferably the chaperone protein complexes have a molecular weight greater than 300 kD. In another embodiment the chaperone protein complexes are purified from the collected IEF fractions. The collected fractions can also be dialyzed. Collected dialyzed fractions can be concentrated by vacuum centrifugation followed by reconstitution of the concentrated fractions.

The present invention also provides for compositions comprised of chaperone proteins, chaperone protein complexes, or aggregates thereof, wherein said chaperone proteins, chaperone protein complexes, or aggregates thereof, are enriched in a biological sample by subjecting the sample to IEF. Said compositions can be used to treat or prevent cancer, or any infectious disease. In a particular embodiment the invention provides a composition comprising a sample enriched in chaperone protein complexes wherein the sample is prepared by a method comprising subjecting a solution comprising chaperone protein complexes and a plurality of different proteins to free solution isoelectric focusing, and collecting one or more fractions with a pH from pH 4.5 to 6.5 wherein at least some of the proteins in the solution are present in fractions other than fractions of pH 4.5 to pH 6.5; wherein the collected fractions comprise a mixture of chaperone protein complexes; and wherein said chaperone protein complexes in said sample are not purified to homogeneity. Preferably, the free solution isoelectric focusing is performed in the presence of urea and detergent. The urea can be present for example in the range of 4M–8M. The detergent can be present for example at concentration in the range of 0.1%–1.7%. The detergent is preferably non-ionic or zwitterionic e.g. octylphenol ethylene oxide condensate, octylphenoxypoly (ethyleneoxy) ethanol, and/or tert-octylphenoxy poly(oxyethylene) ethanol; in a specific embodiment each detergent can be present at 0.1%. The detergents are preferably removed from the fractions collected from FS-IEF, e.g., by dialyzing the collected fractions against a buffer comprising phosphate buffered saline or water.

The present invention also relates to pharmaceutical compositions. Said pharmaceutical compositions are comprised of chaperone proteins, chaperone protein complexes, or aggregates thereof. The pharmaceutical compositions are obtained from a biological sample e.g. animal cells, mammalian cells, or human cells, by subjecting said sample to IEF and obtaining fractions that are enriched in said chaperone proteins, chaperone protein complexes, or aggregates thereof. The biological sample can include a cell lysate. In a preferred embodiment the IEF is FS-IEF. In another embodiment the pharmaceutical composition is obtained by subjecting said sample to FS-IEF and collecting one or more fractions with a pH in the range of 4.5–6.5 wherein said fractions contain a mixture of chaperone protein complexes, or aggregates thereof, and wherein said chaperone protein complexes, or aggregates thereof, are not purified to homogeneity. Said FS-IEF can be performed in the presence of urea, e.g. at a concentration of 4M–8M or 4M–5M, and detergent, e.g. non-ionic and/or zwitterionic. Said collected fractions may be dialyzed against a buffer e.g. phosphate buffered saline. The pharmaceutical compositions obtained by FS-IEF can comprise any chaperone protein, chaperone protein complex, or aggregate thereof, e.g. calreticulin (CRT), gp96, grp75/mt, BiP/grp 78, hsp 90, hsp 72, hsp 60, and hsp70, hsp 40 or any one or more of the foregoing. In a specific embodiment the pharmaceutical composition obtained by FS-IEF comprises GRP94/gp96, hsp 90, hsp 70, and calreticulin. In another specific embodiment, the pharmaceutical composition obtained by FS-IEF comprises GRP94/gp96, hsp 90, hsp 70, hsp 72, hsp 60, hsp 40, calreticulin, BiP/grp 78, and grp75/mt. The pharmaceutical composition obtained by FS-IEF can also comprise noncovalent complexes of chaperone proteins and different peptides. The invention also relates to a kit comprising in one or more containers the pharmaceutical composition obtained by FS-IEF.

The invention also relates to methods of treating or preventing cancer in a subject comprising administering to said subject a therapeutically or prophylactically effective amount of a pharmaceutical composition comprised of FS-IEF enriched chaperone proteins, chaperone protein complexes, or aggregates thereof. The chaperone proteins can be derived from a cell lysate e.g. a lysate of cancer cells of the type of cancer in the subject, or metastasis thereof.

The invention also relates to a method of treating or preventing a type of cancer in a subject, wherein said method comprises subjecting a lysate of cells of a cancer of said type, or metastasis thereof, to FS-IEF; collecting one or more fractions with a pH from pH 4.5 to 6.5 which are enriched in chaperone protein complexes; optionally pooling said collected fractions; and administering said chaperone protein complexes present in said collected fractions to a patient to treat or prevent said cancer. Said subject can be any animal, preferably a mammal, more preferably a human. Said free solution isoelectric focusing can be performed in the presence of urea and detergent. The urea can be present in the range of 4M–8M. The detergent can be present at concentration in the range of 0.1%–1.7%. The detergent can be non-ionic or zwitterionic e.g. octylphenol ethylene oxide condensate, octylphenoxypoly (ethyleneoxy)ethanol, and/or tert-octylphenoxy poly(oxyethylene)ethanol. The detergents can be removed from the fractions collected from FS-IEF prior to use, e.g., by dialyzing the collected fractions against a buffer comprising phosphate buffered saline or water. FS-IEF can be performed in the presence of a salt e.g. sodium chloride. The chaperone protein complexes can be present in aggregates that have a molecular weight that is greater than 100 kD, 200 kD, 300 kD, 400 kD, or 500 kD. The method of the invention further includes combining the chaperone protein complexes obtained in FS-IEF fractions with a biological response modifier e.g. IL-2, IL-4, IL-5, IL-6, IL-12, IL-15, GM-CSF.

The invention also relates to a method of treating or preventing a disease caused by an infectious agent, e.g. a virus, a bacterium, or a parasite, in a subject, wherein said method comprises subjecting a lysate of cells expressing an antigenic molecule displaying antigenicity of an antigen of said infectious agent to FS-IEF; collecting one or more fractions with a pH from pH 4.5 to 6.5 which are enriched in chaperone protein complexes; optionally pooling said collected fractions; and administering said chaperone protein complexes present in said collected fractions to a patient to treat or prevent said disease. Said cell lysate can be of cells transformed with a nucleic acid encoding said antigenic molecule or alternatively the cells can be infected with said infectious agent. Said FS-IEF can be performed in the presence of urea and detergent. The urea can be present in the range of 4M–8M. The detergent can be present at concentration in the range of 0.1%–1.7%. The detergent can be non-ionic or zwittenonic e.g. octylphenol ethylene oxide condensate, octylphenoxypoly (ethyleneoxy) ethanol, and/or tert-octylphenoxy poly(oxyethylene)ethanol. The detergents can be removed from the fractions collected from FS-IEF prior to use. FS-IEF can be performed in the presence of a salt e.g. sodium chloride. The method of the invention includes combining the chaperone protein complexes obtained in FS-IEF fractions for the treatment or prevention of a disease caused by an infectious agent with a biological response modifier e.g. IL-2, IL-4, IL-5, IL-6, IL-12, IL-15, GM-CSF.

The invention also relates to methods of treating or preventing an infectious disease in a subject by administering to said subject a therapeutically or prophylactically effective amount of a pharmaceutical composition comprising FS-IEF enriched chaperone proteins, chaperone protein complexes or aggregates thereof. The chaperone proteins can be derived from a cell lysate e.g. cells expressing an antigenic molecule displaying the antigenicity of an antigen of said infectious agent.

The invention also relates to methods of eliciting an immune response against an antigen in a subject comprising administering to said subject a therapeutically or prophylactically effective amount of a pharmaceutical composition comprising FS-IEF enriched chaperone proteins, chaperone protein complexes or aggregates thereof. Said pharmaceutical composition can be obtained by subjecting a biological sample to FS-IEF and collecting one or more fractions with a pH in the range of 4.5–6.5 wherein said fractions contain a mixture of chaperone protein complexes, or aggregates thereof, and wherein said chaperone protein complexes, or aggregates thereof, are not purified to homogeneity.

In specific embodiments chaperone proteins, chaperone protein complexes or aggregates thereof can be purified to about 30%, 20%, 10%, or 5% (by dry weight) of heterologous protein (also referred to herein as a "contaminating protein").

4. BRIEF DESCRIPTION OF THE FIGURES

Figure 1B:
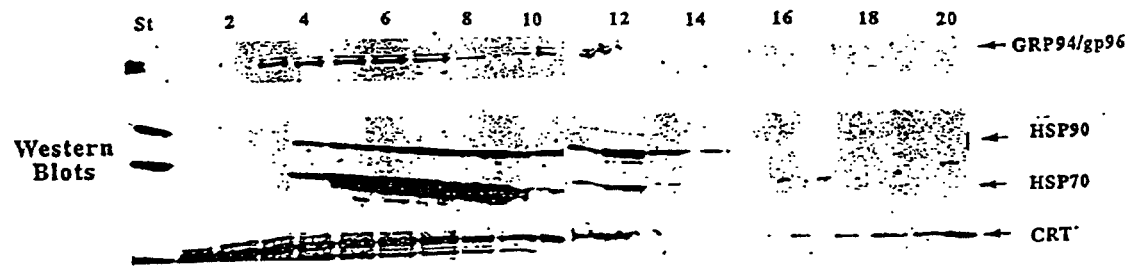

FIGS. 1A–B: Sodium dodecyl sulfate/polyacrylamide gel electrophoresis (SDS-PAGE) and Western Blot of FS-IEF enriched fractions of chaperone proteins. A A20 tumor was homogenized in lysis buffer and a 100,000 g supernatant was obtained. The high speed supernatant was dialyzed into low ionic strength buffer; this preparation was brought to 6 M urea, 5% ampholytes (pH 3–10 and pH 5–8), and 0.5% detergents. The sample was subjected to FS-IEF in a Bio Rad ROTOFOR® cell (Bio-Rad Laboratories, Hercules, Calif.) for 4 hours at 15 W constant power. Twenty fractions were harvested for analysis by SDS-PAGE and stained with Coomassie Blue. Shown are the 20 FS-IEF fractions along with the starting material (St) prior to FS-IEF. Molecular mass markers are indicated to the right. B Following SDS-PAGE, samples were electrotransferred to nitrocellulose and probed with specific antibodies to chaperone proteins grp94/gp96, hsp90, hsp70, and CRT.

Figure 2:
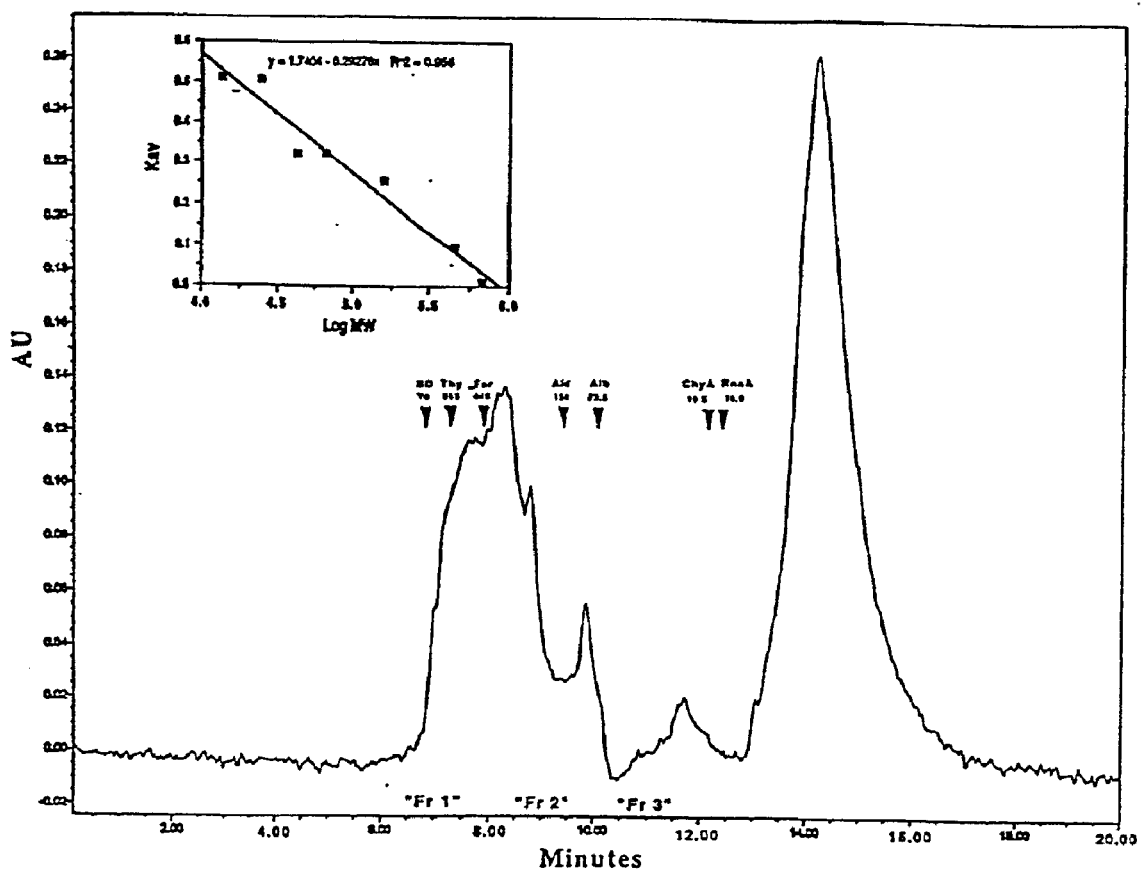
Figure 2:
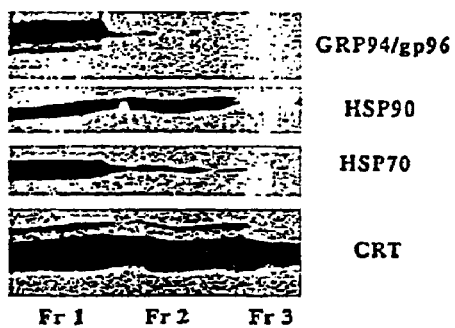

FIG. 2: Size exclusion chromatography demonstrates that FS-IEF enriched fractions of chaperone proteins contain complexes of chaperone proteins.

FIGS. 3A–D: Kaplan-Meier plots for mice immunized with tumor-derived chaperone proteins. Mice were immunized subcutaneously with the indicated vaccines on day 14 and day 7 and received intravenous tumor challenge on day 0. A, B, C Mice received $10^6$ viable A20 cells grown in vivo: D mice were challenged with $10^4$ cells. A Mice (n=6–14/group) were immunized with 20 μg A20 tumor lysate, or with saline. P values: saline versus lysate, not significant (NS); versus FS-IEF, P<0.02. B Mice (n=8/group) were immunized with 20 μg A20-derived FS-IEF fractions with differential protein content, or with saline. FS-IEF$_1$, FS-IEF$_2$ individual fractions from isoelectric focusing that are part of the vaccine pool (e.g., such as that used in A). FS-IEF$^0$ a fraction from the same isofocusing run that is devoid of the four known immunogenic chaperone. P values: saline versus FS-IEF$_0$, NS; versus FS-IEF$_1$, P<0.03; versus FS-IEF$_2$, P<0.02. FS-IEF$_0$ versus FS-IEF$_1$, P<0.05; FS-IEF$_0$ versus FS-IEF$_2$, P<0.04. FS-IEF$_1$ versus FS-IEF$_2$, NS. C Mice (n=7–14/group) were immunized with 20 μg tumor-derived FS-IEF material or with 20 μg tumor-derived, purified hsp70, or with saline. P values: saline versus FS-IEF, P<0.002; versus hsp70, P<0.002; FS-IEF versus hsp70, NS. D Mice (n=12/group) were immunized with increasing quantities (20 μg–200 μg) of A20-derived FS-IEF material, or with saline. For clarity, only data from immunizations with 20, 50, and 100 μg vaccine are shown. P values: saline versus 20 μg FS-IEF, P<0.04 versus 50 μg or 100 μg FS-IEF. P values for saline versus 75 μg or 200 μg FS-IEF vaccinations were also NS.

Figure 4:
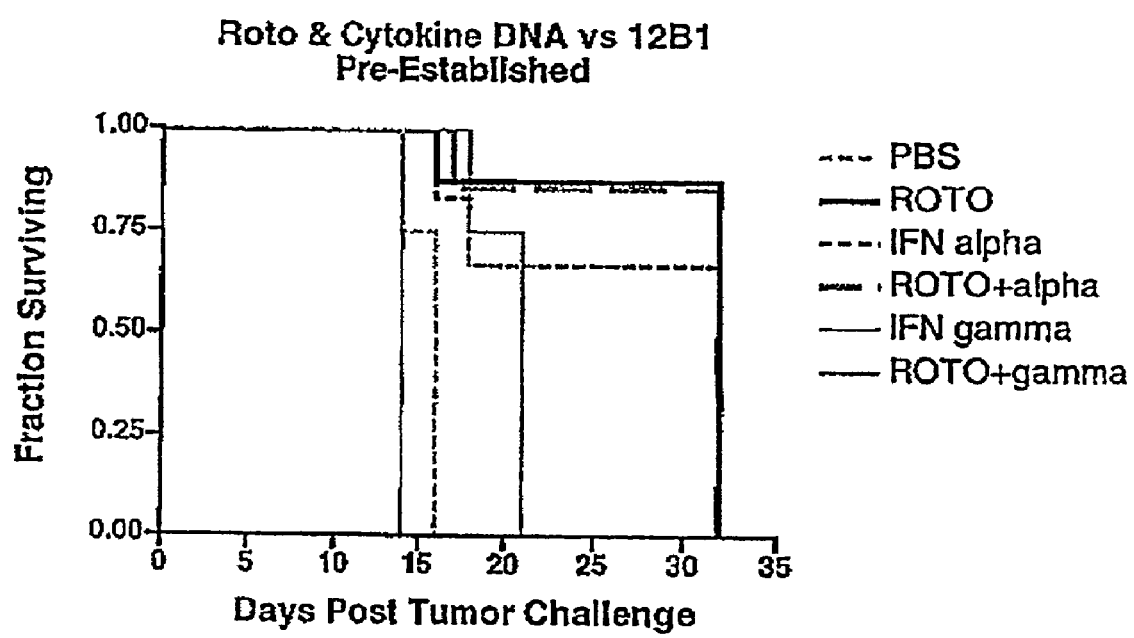

FIG. 4: Survival of mice with pre-established 12B1 tumors. Mice were treated with cDNA encoding cytokines interferon alpha or interferon gamma 2 days post inoculation with 12B1 tumor cells followed by treatment with 20 μg of enriched chaperone protein complexes derived from 12B1 tumors. Chaperone proteins or chaperone protein complexes were enriched using the ROTORFOR® device (Bio-Rad Laboratories, Hercules, Calif.) with a pH gradient established using ROTOLYTES® (Bio-Rad Laboratories, Hercules, Calif.).

Figure 5:
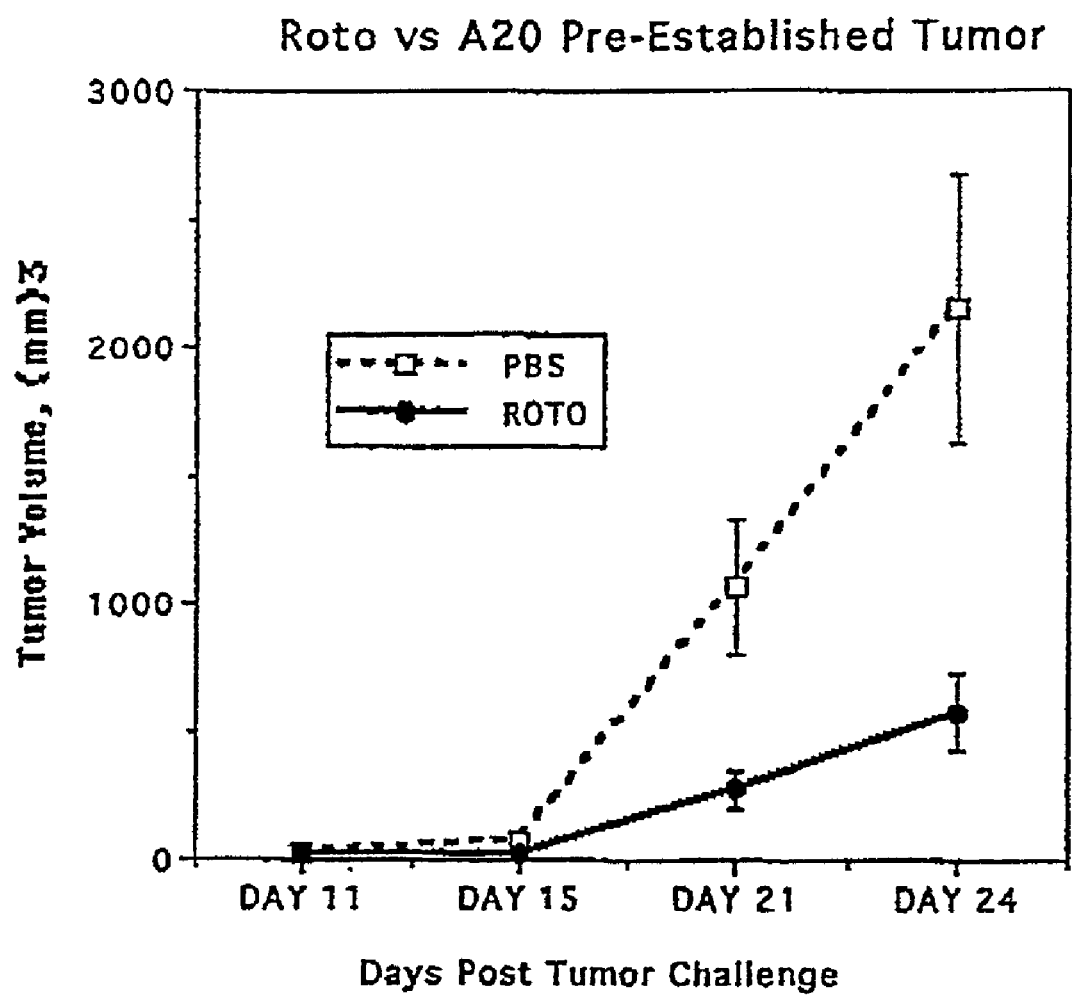

FIG. 5: Tumor volume in mice inoculated with 500,000 A20 tumor derived cells subcutaneously and subsequently treated, on day 6, and day 12 post tumor inoculation, with A20-derived chaperone protein complexes. The A20-derived chaperone protein complexes were prepared using the ROTORFOR® device (Bio-Rad Laboratories, Hercules, Calif.) with a pH gradient established using ROTOLYTES® (Bio-Rad Laboratories, Hercules, Calif.). Tumor volume in mice receiving phosphate buffered saline (PBS, negative control) is shown for comparison.

5. DETAILED DESCRIPTION OF THE INVENTION

The present invention provides methods for recovering chaperone proteins and chaperone protein complexes in one step from a mixture of cellular proteins. The methods of the invention involve the use of isoelectric focusing (IEF). In preferred embodiments of the invention, IEF is performed in an appropriate buffer and a system of ampholytes. The preferred technique is known as free solution isoelectric focusing (FS-IEF).

The methods of the invention can be used to recover chaperone and chaperone protein complexes that include but are not limited to gp96, the hsp90 isoforms hsp86 and hsp84, the hsp70 isoforms hsp70 and hsc70, hsp60, and hsp40, and calreticulin (CRT) and complexes thereof. Such complexes appear to be present in aggregates or in multimeric forms, and are encompassed by the invention. The methods of the invention can also be used to prepare a vaccine composition wherein the chaperone protein complexes recovered by the methods comprise antigenic and/or immunogenic molecules.

Chaperone proteins are generally capable of associating with other molecules, such as proteins or peptides to form chaperone protein-protein complexes. The term "chaperone protein-protein complex" or "chaperone protein complex" encompasses a molecular complex of chaperone protein and another protein. The protein can be denatured or non-denatured. The protein associated with the chaperone protein in a chaperone protein complex can be a naturally occurring protein, a protein produced by a genetically engineered cell, or a synthetic protein. The proteins can become associated with chaperone proteins inside a cell, i.e., endogenously. Inside a cell, the protein is noncovalently associated with a chaperone protein. Under the appropriate conditions, a chaperone protein can also become associated with a protein in a reaction in vitro, i.e., exogenously. The methods of the invention can be used to recover chaperone protein complexes comprising noncovalently associated proteins, as well as covalently linked proteins.

Chaperone proteins are among the most highly conserved proteins in existence. For example, DnaK, the hsp70 from E. coli has about 50% amino acid sequence identity with hsp70 proteins from eukaryotes (Bardwell, et al., 1984, Proc. Natl. Acad. Sci. 81:848). The hsp60 and hsp90 families also show similarly high levels of intrafamilies conservation (Hickey, et al. (1989) Mol. Cell. Biol. 9:2615; Jindal (1989) Mol. Cell. Biol. 9:2279). Because chaperone proteins are so highly conserved, the methods of the invention are applicable to homologous chaperone proteins in many species of organisms including bacteria, fungi, plants, and animals. Preferably, the chaperone proteins recovered by the methods of the invention are mammalian chaperone proteins. More preferably, the chaperone proteins are human chaperone proteins.

The methods of the invention are particularly useful for the manufacture of vaccines comprising autologous chaperone protein complexes. In this context, the ability to obtain compositions enriched for gp96, hsp86/84, and hsc70 complexes and other chaperone protein complexes from the same tumor sample provides a new type of vaccine. It also allows the testing of the effect of a synergistic immunization with multiple chaperone protein complexes. The respective immunogenicity of each chaperone protein complex can be tested under conditions where the different chaperone protein vaccines are truly comparable as they are derived from an identical source. These studies will also permit one to look comparatively and sequentially into the intracellular trafficking of proteins that are bound by these chaperone proteins.

Previously available methods for purification of immunogenic chaperone protein and chaperone protein complexes from a sample have led to the isolation of a unique chaperone protein species while neglecting the rest of the sample that might be used as a complementary source of chaperone protein-based vaccine. For example, Concanavalin A (ConA) column that retains gp96 as a first chromatographic step is not useful for hsp70, hsp90, and calreticulin purification. See Menoret and Bell (2000) *J. Immun. Methods* 237(1–2):119.

The present invention provides for methods to isolate aggregates of chaperone proteins and chaperone protein complexes. The aggregates have an apparent molecular weight of greater than 300 kilodaltons when determined by size exclusion chromatography. The aggregates can have a molecular weight in the range of 300–500 kilodaltons, or the aggregates can have a molecular weight greater than 500 kilodaltons. The aggregates may comprise different chaperone proteins and/or chaperone protein complexes. As an example, but not as a limitation, the aggregates may comprise any or all of the following: GRP94/gp96, HSP90, HSP70, and CRT and complexes thereof.

The methods described herein have several advantages over previously available methods of isolating chaperone protein and chaperone protein complexes. The inventors of the present invention have discovered that FS-IEF enriched fractions of tumor derived chaperone proteins and complexes provide better protection than individually purified chaperone proteins and complexes against subsequent challenge with cells derived from the same type of tumor. Hence, purification of chaperone-protein complexes to homogeneity is not required for the preparation of vaccines, thus saving time in the preparation of the vaccine and reducing sample loss due to multiple purification steps. FS-IEF is a rapid, efficient method for the recovery of enriched fractions containing chaperone protein complexes in therapeutic amounts from biological samples.

The use of FS-IEF has the advantage over other IEF methods in that large quantities of sample can be separated or enriched. Hence, milligram quantities of enriched chaperone proteins and complexes can be obtained from a gram of starting material. The following sections describe in details the enrichment of multiple chaperone protein complexes from a sample by IEF, and the preparing and use of a vaccine based on chaperone protein complexes prepared by IEF.

5.1. Enrichment of Chaperone Proteins and Complexes

Separation of proteins by isoelectric focusing is based on the fact that all proteins have a pH-dependent net charge. The net charge is determined both by the amino acid sequence of the protein and the pH of the environment. When a protein is electrophoresed through an established pH gradient, it will migrate until it reaches the pH where the net charge on the protein is zero; at that point it will stop migrating and is said to be focused at its isoelectric point (pI).

A protein with a net positive charge, for example, in a particular region of the pH gradient will tend to migrate toward the cathode while concurrently giving up protons. At some point, the net charge on the molecule will be zero and the protein will cease to migrate. If the protein diffuses into a region of net charge, the resultant electrical force on it will drive it back to its pI, so that the molecule becomes focused at the point.

In practice, isoelectric focusing involves the application of an electric voltage to an appropriate matrix that contains charged buffer molecules, such that the charged buffer molecules form a pH gradient within the matrix. When a sample of proteins is added to the matrix, the proteins migrate within the matrix to a point in the established pH gradient where the protein has no net charge. Ampholytes which are small, charged buffer molecules are commonly used to establish the pH gradients increasing in pH from anode to cathode. When voltage is applied to a system of ampholytes and proteins, all the components migrate to their respective pIs. Ampholytes rapidly establish the pH gradient and maintain it for long periods allowing the slower moving proteins to accumulate or focus. It is contemplated that other small charged molecules could be used to establish a pH gradient.

The methods of the invention comprises subjecting a sample comprising chaperone proteins and/or chaperone protein complexes to isoelectric focusing under the appropriate conditions and for a sufficient period of time such that chaperone proteins and chaperone protein complexes with similar isoelectric points migrate to similar regions along the pH gradient, and collecting the chaperone proteins and chaperone protein complexes that have accumulated at various regions in the pH gradient.

The methods of the invention are typically performed in an apparatus designed for isoelectric focusing, and preferably for free solution isoelectric focusing. An example of such an apparatus is the ROTOFOR® system by Bio-Rad Laboratories (Hercules, Calif.).

In one embodiment, the present invention provides a method for enriching for chaperone proteins and chaperone protein complexes from a mixture, for example, from a lysate of cells. The cell lysate, or a fraction of a cell lysate, can be prepared by any means known in the art. For example, the cell lysate can be prepared using mechanical means such as, but not limited to, a dounce homogenizer, a motor driven glass teflon homogenizer or by use of a French press. The glass teflon homogenizer can be cooled by any means known in the art. Alternatively, the lysate can be prepared by sonication; or by chemical means such as use of detergents or a hypotonic or hypertonic buffer.

A preferred, exemplary protocol for preparing a cell lysate is provided hereinbelow:

Cells are homogenized by a motor driven glass teflon homogenizer at 40° C. in a buffer consisting of 10 mM Tris/Cl (pH 7.4), 10 mM NaCl, 0.1% octylphenol ethylene oxide condensate, 0.1% octylphenoxypoly (ethyleneoxy) ethanol, 0.1% tert-octylphenoxy poly(oxyethylene)ethanol, leupeptin (2 ug/ml), pepstatin A (1 ug/ml), phenylmethylsulfonylfluoride (0.5 mM), and one complete protease inhibitor cocktail tablet (Roche Molecular Biochemicals, Indianapolis, Ind.). The cell lysate is then first centrifuged at 10,000 g for 20–30 minutes at 4° C. followed by harvesting the supernatant, and then further ceutrifuged at 100,000 g for 60–90 minutes at 40° C. followed by harvesting the supernatant.

The supernatant is dialyzed against a buffer consisting of 5 mM Tris/Cl (pH 7.4), 5 mM NaCl, 0.05% octylphenol ethylene oxide condensate, 0.05% octylphenoxypoly (ethyleneoxy) ethanol, 0.05% tert-octylphenoxy poly(oxyethylene)ethanol. The supernatant is then dialyzed against a buffer consisting of 2.5 mM Tris/Cl (pH 7.4), 2.5 mM NaCl, 0.025% octylphenol ethylene oxide condensate, 0.025% octylphenoxypoly (ethyleneoxy) ethanol, 0.025% tert-octylphenoxy poly(oxyethylene)ethanol. The supernatant is next dialyzed against a buffer consisting of 1.25 mM Tris/Cl (pH 7.4), 1.25 mM NaCl, 0.012% octylphenol ethylene oxide condensate, 0.012% octylphenoxypoly (ethyleneoxy) ethanol, 0.012% tert-octylphenoxy poly(oxyethylene)ethanol. The supernatant is finally dialyzed into water. The compositions of the various buffer and centrifugation conditions provided herein are not intended to be limiting. Various modifications of the lysis buffer, dialysis buffer, centrifugation parameters can be made by those skilled in the art in view of practical considerations.

In an alternative embodiment of the invention the supernatant is dialyzed directly against a buffer consisting of 1.25 mM Tris/Cl (pH 7.4), 1.25 mM NaCl, 0.012% octylphenol ethylene oxide condensate, 0.0 12% octylphenoxypoly (ethyleneoxy) ethanol, 0.012% tert-octylphenoxy poly (oxyethylene)ethanol and then into water.

Prior to IEF, a sample comprising chaperone proteins and chaperone protein complexes is added to a preformed pH gradient or mixed with a matrix comprising charged buffer molecules or ampholytes that form a pH gradient in the presence of an electric field. Any matrix and any ampholytes known in the art for IEF or FS-IEF can be used. For example, ampholytes by Sigma can be used (Sigma, St. Louis, Mo.). In a preferred embodiment, the charged buffer molecules are ROTOLYTES® (Bio-Rad Laboratories, Hercules, Calif.). The setting up of the pH gradient is dependent on the choice and proportions of charged buffer molecules or ampholytes used. A pH gradient of pH 2 to pH 11 can be used for the methods of the invention. Preferably, the acidic end of the pH gradient is at about pH 3 to pH 4, and the alkaline end of the pH gradient is at about pH 8 to pH 10. Most preferable is a pH gradient that can resolve proteins with isoelectric points within the range of about pH 4.0 to pH 7.0. Thus, depending on the type of charged buffer molecules or ampholytes used to form the pH gradient, the relative amounts of charged buffer molecules or ampholytes, matrix components and protein sample can be determined empirically by one skilled in the art or by following instructions provided with the ampholytes, or the IEF or FS-IEF apparatus.

In one embodiment the dialyzed supernatant is prepared for FS-IEF by filtering it through a 8 μm filter.

In a specific embodiment solubility of the proteins in the supernatant is maintained by the addition of detergents, and urea, and preferably salt (e.g. sodium chloride), and ampholytes or other charged particles to the supernatant prior to FS-IEF. In such embodiment the concentration of urea in the supernatant that is applied to the FS-IEF apparatus is in the range of about 4M–8M. The concentration of detergent in the supernatant that is applied to the FS-IEF apparatus is preferably in the range of about 0.1%–1.7%. Any detergent can be used that prevents the precipitation of the proteins in the supernatant during FS-IEF. Preferably the detergents are zwitterionic or non-ionic detergents. Most preferably the detergents are octylphenol ethylene oxide condensate, octylphenoxypoly (ethyleneoxy) ethanol and/or tert-octylphenoxy poly(oxyethylene)ethanol. The detergents can be combined in any concentration so long as the final concentration is preferably 0.1%–1.7%. As an example, but not as a limitation, octylphenol ethylene oxide condensate, octylphenoxypoly (ethyleneoxy) ethanol, and tert-octylphenoxy poly(oxyethylene)ethanol can be used each at a concentration of about 0.1%. Alternatively, if detergent remains in the supernatant after dialysis at a concentration that is sufficient to prevent precipitation of the proteins during FS-IEF, then no additional detergent need be added to the supernatant prior to FS-IEF.

A preferred, exemplary FS-IEF protocol involves filtering the dialyzed supernatant described above through an 8 μm filter and bringing the filtrate to a concentration of 6 M urea, 0.5% octylphenol ethylene oxide condensate, 0.5% octylphenoxypoly (ethyleneoxy) ethanol, 0.5% tert-octylphenoxy poly(oxyethylene)ethanol, and 5% ampholytes (in the ratio of 2 parts pH 5–8 and 1 part pH 3–10). A high concentration of detergent, urea, and ampholytes is preferred so as to maintain protein solubility during JIEF or FS-IEF.

The samples comprising chaperone proteins and/or chaperone protein complexes are subjected to IEF or FS-IEF which is conducted within an apparatus for a time sufficient for the pH gradient to form and for the proteins in the sample to migrate or to be electrophoresed to a point in the pH gradient where there is no net charge on the proteins. Typically, 2 to 5 hours are sufficient for the protein to reach its position within the pH gradient where it will stop migration. The apparatus comprises an acidic buffer in a compartment at the anode and a basic buffer contained in a compartment at the cathode. The voltage applied across the electrodes is at a level sufficient to set up a pH gradient and to cause charged protein molecules to migrate through the matrix, and can range from 500 V to 2000 V, and more preferably 700 V to 1200 V. To prevent denaturation of the proteins, and to prevent damage to the apparatus, it is preferred to keep the temperature low at about 4° C. To control temperature within the apparatus, a cooling means (such as recirculating water) and/or a limit on the power output of the power supply can be applied.

Accordingly, in a preferred embodiment of the invention, 0.1 M $H_3PO_4$ is used as the buffer in the anode compartment of the apparatus and 0.1 M NaOH in the cathode compartment of the apparatus. FS-IEF is conducted in a ROTOFOR® apparatus (Bio-Rad Laboratories, Hercules, Calif.) wherein an electric field having a constant power of about 15 Watts is applied for about 4 hours at a constant temperature of 4° C.

After the sample has been electrophoresed through an appropriate matrix, such that the chaperone proteins and chaperone protein complexes reach their respective pI's, fractions containing the chaperone proteins and chaperone protein complexes are collected. Where the matrix is a solid or gel, the chaperone proteins and complexes can be eluted into an appropriate buffer. Preferably fractions are collected that contain grp94/gp90, and hsp90, and hsp70 and CRT and pooled. The sample fractions can also contain additional proteins such as, but not limited to, hsp73, BiP/grp78, grp75/mt hsp70, and hsp72. Where the matrix is a liquid, fractions can be separately collected by applying to a region within the matrix an external force, such as, but not limited to, a vacuum, or through the use of centrifugal force or gravity. Fractions containing chaperone proteins or chaperone protein complexes can be pooled together.

In one embodiment the invention comprises chaperone proteins or chaperone protein complexes that are enriched from a cell lysate by IEF. Hence the enriched chaperone proteins or chaperone protein complexes include cytosolic chaperone proteins or chaperone protein complexes. The chaperone proteins or chaperone protein complexes can be present in one or more IEF fractions. In a preferred embodiment the fractions contain a plurality of proteins so that the chaperone proteins or chaperone protein complexes are enriched, but are not purified to homogeneity. Purity can be assessed by any method known in the art, but PAGE analysis is preferred. The chaperone proteins complexes or aggregates thereof obtained by IEF will preferably have a molecular weight greater than 300 kD. In one embodiment the chaperone protein complexes will have a molecular weight in the range of 300–500 kD.

Collected fractions that comprise chaperone proteins and/or chaperone protein complexes can be identified by analyzing said fractions by a variety of methods, such as SDS-PAGE and Western Blot. Western Blot can be performed using a primary antibody that binds specifically to the chaperone protein or chaperone protein complex of interest. The primary antibody can be conjugated to an appropriate label to provide detection of said chaperone protein or chaperone protein complex. Alternatively, a secondary antibody conjugated to an appropriate label can be used to detect the chaperone protein or chaperone protein complex of interest. Primary antibodies that recognize chaperone proteins can be obtained from commercial suppliers such as Stressgen Biotechnologies Corp. (British Columbia, Canada) or made by standard methods.

As shown in the Examples in Section 6, fractions collected from the pH gradient that comprise detectable amounts of chaperone proteins and chaperone protein complexes falls within a range of pH from pH 4.5 to 6.5. Fractions collected from the pH gradient having a pH of 5.4 to 6.4 are preferred as they contain high concentrations of chaperone proteins and chaperone protein complexes, in particular, calreticulin, hsp70, grp94/gp96, and hsp90. Selected fractions from the pH gradient can be pooled prior to further processing or purification. Due to the highly conserved amino acid sequences of chaperone proteins among different species, the pH range in which chaperone proteins and complexes from other species will accumulate is not expected to vary widely between species. Thus, the pH ranges of the methods of the invention can be used with any chaperones, including bacterial chaperones, mammalian chaperones, and human chaperones.

Chemicals, such as but not limited to, ampholytes or other charged buffer particles, detergents, or urea are present in the pH gradient fractions and are generally undesirable. Such chemicals can be substantially removed, and chaperone proteins and/or chaperone protein complexes recovered from the pH gradient fractions by dialysis, chromatography, or other methods known in the art. Thus, in one embodiment fractions containing chaperone proteins or chaperone protein complexes are dialyzed first into 2M urea in 0.1×PBS and then into 0.1×PBS. Alternatively, fractions containing chaperone proteins or chaperone protein complexes can be dialyzed directly into 0.1×PBS. Detergents can be removed from the sample by any means known in the art. As an example, but not as a limitation, detergents can be removed by applying the sample containing the chaperone proteins or chaperone protein complexes to an Extracti Gel D Column® (Pierce Endogen, Rockford, Ill.). The resulting compositions are enriched with chaperone proteins and/or chaperone protein complexes and substantially free of chemicals used in the methods of the invention.

Depending on the fraction and whether selected fractions are combined, the compositions of the invention comprise a plurality of chaperone proteins and/or chaperone protein complexes, and the relative amounts of individual chaperone proteins and/or chaperone protein complexes may vary. Moreover, as described in Section 6.2, the chaperone proteins and/or chaperone protein complexes present in such compositions are present not only as monomers but also as high molecular weight multimers or aggregated forms.

It has been shown that preparations of gp96, hsp70, hsp86/84, and CRT complexes can be used as vaccines against tumors and infectious diseases. Recently, it has also been shown that hsp110 and grp170 and complexes thereof can used as effective vaccines (Wang et al., 2001, *J. Immun.* 166:490). Thus, the methods of the invention can be used to prepare such vaccines. According to the methods of the invention, pH gradient fractions enriched for gp96, hsp70, hsp90, CRT, hsp110, and grp170 can be identified for use directly or after dialysis, concentration and reconstitution. Fractions enriched for gp96, hsp70, hsp90, CRT, hsp110, and grp170 can also be processed further to obtain purified preparations. Accordingly, the invention provides methods for enrichment of gp96, hsp70, hsp90, CRT, hsp110, and grp170 complexes from a cell sample, and compositions enriched with gp96 complexes, with hsp70 complexes, with hsp86/84 complexes, with CRT complexes, hsp110 complexes or grp170 complexes.

Chaperone proteins, such as those described above, that have been genetically engineered can also be recovered by the methods of the invention. Examples of modified chaperone proteins, and complexes thereof are described in WO 99/42121.

In another embodiment, IEF can be combined with other methods for purification of chaperone proteins and chaperone protein complexes. According to the invention one or more of the collected fractions enriched for a particular chaperone protein and/or complexes thereof can be used as a source for further purification of the chaperone protein or complexes. It is contemplated that IEF can be used in combination with methods well known in the art for the purification of chaperone proteins and/or chaperone protein complexes to homogeneity, including but not limited to ADP affinity chromatography, Concanavalin A chromatography, heparin chromatography, or ion exchange chromatography such as anion exchange chromatography, cation exchange chromatography or DEAE chromatography.

In a specific embodiment, after IEF, the fractions comprising hsp60 or hsp60 complex are pooled for further purification using methods well known in the art, such as ATP affinity chromatography (Vittanen (1992) *J. Biochem.* 267:695).

In another embodiment of the invention, after IEF, one or more fractions comprising hsc70 or hsc70 complex are used, pooled if necessary, for further purification using methods well known in the art. For example, hsc70 fractions from IEF separation are pooled and applied to ADP affinity chromatography. The resulting fractions can be further purified using ion exchange chromatography. (See Menoret and Bell (2000) *J. Immun. Methods* 237(1–2):119; see also U.S. Pat. No. 5,837,251.) Therefore, the invention provides a method for purifying hsc70 or hsc70 complex from a sample comprising hsc70 or hsc70 complex, said method comprising IEF followed by ADP affinity chromatography, and optionally ion exchange chromatography purification.

In another embodiment of the invention, after IEF, the fractions comprising hsp84 or hsp84 complex are pooled for further purification using methods well known in the art. In another embodiment of the invention, after IEF, the fractions comprising hsp86 or hsp86 complex are pooled for further purification using methods well known in the art. For example, fractions containing hsp90 (which includes hsp 84 and hsp86) collected from IEF are pooled and applied to anion exchange chromatography. Purified hsp90 or hsp90 complexes are eluted in the presence of buffer with a concentration of about 440 to 590 mM NaCl. (See Menoret and Bell (2000) *J. Immun. Methods* 237(1–2):119; see also U.S. Pat. No. 5,837,251.) Therefore, the invention provides a method for purifying hsp90 from a sample comprising hsp90 or hsp90 complex, said method comprising IEF followed by anion exchange chromatography.

In yet another embodiment of the invention, after IEF, the fractions comprising gp96 or gp96 complex are pooled for further purification using methods well known in the art. For example, according to a preferred embodiment, gp96 fractions from IEF separation are pooled and applied to Concanavalin A (ConA) chromatography. The resulting fractions comprising gp96 or gp96 complex are further purified by ion exchange chromatography. (See Menoret and Bell (2000) *J. Immun. Methods* 237(1–2):119; see also U.S. Pat. No. 5,837,251.) Therefore, the invention provides a method for purifying gp96 or gp96 complex from a sample comprising gp96 or gp96 complex, said method comprising IEF separation followed by Con A chromatography and ion exchange chromatography purification.

In yet another embodiment of the invention, after IEF, the fractions containing hsp40 or hsp40 complex are pooled for further purification using methods well known in the art.

In yet another embodiment of the invention, after IEF, the fractions containing hsp70 or hsp70 complex are pooled for further purification using methods well known in the art, such as ADP affinity chromatography (Peng et al. (1997) *J. Immun. Meth.* 204:13).

In yet another embodiment the invention provides a kit comprising at least one of the following: ampholytes, premixed ampholytes, electrophoresis buffers, cell solubization buffers, loading buffers and an IEF apparatus; and instructions on the use of the reagents and/or the apparatus in the kit to perform IEF to enrich for chaperone proteins or chaperone protein complexes. Optionally, the kit may further comprise buffers and cell samples comprising recoverable amounts of chaperone proteins or chaperone protein complexes, or detectably labeled chaperone protein or chaperone protein complexes. The kit can be used for screening for the presence of chaperone protein complexes in a biological sample. The kit can also be used for screening for a pharmaceutical composition comprised of chaperone protein complexes or aggregates thereof in a biological sample.

The methods of the invention can be used to enrich chaperone proteins or chaperone protein complexes that effectively stimulate an immune response in a subject against the antigen associated with the chaperone. The methods of the invention can readily be scaled up to accommodate the recovery of chaperone proteins or chaperone protein complexes from large-volume sample, e.g., when cell culture supernatant or fermentation broth is used, or large number of samples, e.g., when many clinical samples are to be processed rapidly or simultaneously. Optimization and/or automation of the methods for use in large scale batch or continuous processes, or high turnover parallel operations are also contemplated.

5.1.2. FS-IEF Enrichment of Chaperone Proteins and Complexes Using a Rotofor Device In a preferred embodiment of the invention, chaperone proteins or chaperone Protein complexes are enriched by FS-IEF using a ROTORFOR® device (Bio Rad Laboratories, Hercules, Calif.) as described by way of example infra.

5.2. Preparation of Vaccines Comprising Multiple Chaperone Protein Complexes The non-covalent association of chaperone proteins with peptides is preserved during FS-IEF, and elution or recovery. As shown in the working examples, presented herein in Section 6.1, the peptides remain non-covalently associated with the chaperone proteins during isoelectric focusing. Accordingly, in one embodiment, it is contemplated that this method can be used in the concomitant preparation of multiple vaccines based on separately purified immunogenic chaperone protein complexes. In another embodiment the methods of the invention can be used to prepare a vaccine that comprises immunogenic complexes of proteins with multiple different chaperone proteins including aggregated complexes.

The multiple chaperone proteins or chaperone protein complexes can be readily obtained from cancer cells or cells infected by an infectious agent or other antigenic cells by an efficient one-step IEF enrichment method and prepared as vaccines. The multiple chaperone proteins or chaperone protein complexes can also be obtained from cells displaying the antigenicity of an infectious agent or alternatively a cell that has been transfected or transformed with one or more genes that encode antigens of an infectious agent. The vaccine or therapeutic compositions so recovered are useful for treatment or prevention of diseases, such as cancer, infectious diseases, and autoimmune diseases.

The present invention relates to vaccine formulations suitable for administration to humans, as well as veterinary uses. The vaccines of the present invention may be designed for administration to any mammal including, but not limited to, domestic animals, such as cats and dogs; wild animals, including foxes and racoons; livestock and fowl, including horses, cattle, sheep, turkeys and chickens. The present invention also relates to vaccine formulations suitable to administration to any rodent.

According to the invention, a method is provided for preparing a vaccine composition by IEF said method comprising the steps of placing a sample, such as a lysate of cells, comprising immunogenic or antigenic chaperone proteins or chaperone protein complexes in an appropriate matrix with a buffer containing charged buffer particles, for example ampholytes, and applying an electric field to said matrix, such that the charged buffer particles form a pH gradient, and said antigenic chaperone proteins or chaperone protein complexes migrate through the matrix until they reach a position where they cease to migrate, and collecting and recovering the desired immunogenic chaperone proteins or chaperone protein complexes under appropriate conditions. In a preferred aspect, the invention provides a method for preparing a vaccine composition comprising chaperone proteins or chaperone protein complexes derived from the patient to whom the vaccine is administered wherein said method utilizes IEF for enrichment of said chaperone proteins or chaperone protein complexes. The patient's enriched chaperone proteins or chaperone protein complexes can be collected from the pH gradient established by IEF under appropriate conditions and administered back into the same patient.

According to the invention, a method is provided for preparing a vaccine composition by IEF wherein said vaccine composition is comprised of a chaperone protein or chaperone protein complex derived from a source that is autologous or allogeneic to the subject receiving the vaccine composition.

As set forth in detail in section 5.2.1 to follow, the methods of the invention can be used to recover chaperone proteins and chaperone protein complexes from a variety of cells. The methods may be used to recover chaperone proteins or chaperone protein complexes from any eukaryotic cells, for example, tissues, isolated cells or immortalized eukaryotic cell lines infected with a pathogen, tumor cells or tumor cell lines, and eukaryotic cells transfected with a gene encoding and expressing a tumor-specific antigen, tumor-associated antigen or an antigen of the pathogen. The recovered mixture of chaperone protein complexes may be stored or combined with a pharmaceutically acceptable carrier to form a pharmaceutical composition suitable for administration as a vaccine. The methods of the invention are particularly useful when the amount of one type of chaperone protein complexes recovered from a limited sample is insufficient. In another aspect, the mixture of chaperone protein complexes recovered from a cell sample may be further purified to prepare a vaccine composition. It is contemplated that the methods of the invention will provide for the development of vaccines based on individual or multiple chaperone protein complexes recovered from cell samples which are available only in limited amounts. In yet another aspect, the presence of aggregated forms or multimers of chaperone protein complexes in a vaccine composition of the invention may have particular benefits, such as smaller dosages.

It is further contemplated that the antigenic chaperone protein complexes will typically be isolated directly from tumor tissue excised from the animal that is to be treated. Alternatively the antigenic chaperone protein complexes can be isolated from any established cell line known in the art. As a non-limiting example the antigenic chaperone protein complexes can be isolated from any cancer cell line or alternatively the antigenic chaperone protein complexes can be isolated from a cell line infected with an infectious agent. As an example, but not as a limitation, the infectious agent could be a virus.

In a preferred embodiment of the invention, the chaperone protein complex is isolated from the cancer cells or precancerous cells of each individual patient (e.g., preferably prepared from infected tissues or tumor biopsies of the patient.) Under certain conditions, however, the amount of tumor tissue available for isolation of the complex may be limiting. Accordingly, it is contemplated that the excised tumor tissue would be used more efficiently using FS-IEF which can enrich in one step a mixture of chaperone protein complexes from such a limited sample. The methods of the invention are advantageous in these circumstances because it circumvents the sample size limitation, and provides the possibility of using multiple chaperone protein complexes synergistically in eliciting immunity.

In a preferred aspect of the invention, the method will be used to enrich and recover chaperone proteins or chaperone protein complexes with particular utility as vaccines for human infectious diseases or cancers. However, it is appreciated that the method described herein will also be useful in enriching and recovering chaperone proteins and chaperone protein complexes from animals in general, for example, mammals, non-human animals such as farm animals including, but not limited to: cattle; horses; goats; sheep; pigs; etc. and household pets including, but not limited to: cats; dogs; etc. The method can be used to enrich and recover chaperone proteins or chaperone protein complexes from birds or poultry. The method can also be used to enrich and recover naturally occurring and/or recombinant chaperone proteins from either prokaryotic or eukaryotic organisms (e.g., primary tissue samples) or cells that have been grown in culture (e.g., cell lines). The method can be used to enrich and recover immunogenic or antigenic aggregates of chaperone proteins and chaperone protein complexes.

5.2.1. Sources of Chaperone Proteins and Chaperone Protein Complexes

The source from which chaperone proteins and chaperone protein complexes are recovered may be selected on the basis of the intended use of the resulting chaperone proteins or chaperone protein complexes. Since chaperone proteins and chaperone protein complexes are found in all cells, any tissue or cell sample can be used as a source. Thus, the tissue of any animal can serve as the source of chaperone proteins and chaperone protein complexes. Alternatively, any continuous or primary cell line known in the art can serve as the source of chaperone proteins and chaperone protein complexes. Chaperone proteins and chaperone protein complexes can also be released from cells (e.g., by necrotic cell death) into the cells' surroundings; thus body fluids, secretions, culture supernatant, fermentation broth, and the like can be a source from which chaperone proteins and chaperone protein complexes are recovered by the methods of the invention.

For the treatment or prevention of infectious diseases or cancer, the invention provides methods for recovering antigenic or immunogenic chaperone protein complexes from infected cells or cancer cells, wherein said chaperone protein complexes can be administered to induce an immune response against the infected cells or the cancer cells. Infected and cancerous cells can also be prepared in vitro from noncancerous or uninfected cells (e.g., normal cells), as appropriate by methods known in the art. (See for example U.S. Pat. No. 6,017,540, which is incorporated by reference herein in its entirety.) In preferred embodiments, the chaperone proteins and chaperone protein complexes are enriched from cancer or infected tissues, cells, or cell lines, all of mammalian origin. In a most preferred embodiment, the cancer or infected tissues, cells, or cell lines are of human origin.

In one embodiment of the invention, for applications relating to treatment and prevention of infectious diseases, the antigenic chaperone protein complexes can be recovered from any infected cell, including; whole tissues, isolated cells, and immortalized cell lines infected or transformed with an intracellular pathogen. The antigenic chaperone protein complexes can be recovered from cells infected with an infectious agent, and in particular with an intracellular pathogen. It has been demonstrated that a vaccine containing antigenic chaperone protein complexes isolated from cells infected with an intracellular pathogen and then administered to a mammal can effectively stimulate cellular immune responses against cells infected with the same pathogen. Specifically, the immune response is mediated through the cytotoxic T cell cascade which targets and destroys cells containing intracellular pathogens. An intracellular pathogen is any viable organism, including, but not limited to, viruses, bacteria, fungi, protozoa and intracellular parasites, capable of existing within a mammalian cell and causing a disease in the mammal.

In another embodiment of the invention, antigenic chaperone protein complexes can be recovered from cells infected with viruses including, but not limited to, hepatitis type A, hepatitis type B, hepatitis type C, influenza, varicella, adenovirus, HSV-1, HSV-II, rinderpest rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, HIV-I, and HIV-II. In addition, antigenic chaperone protein complexes can also be collected from cells transfected with a viral gene.

In another embodiment of the invention, the antigenic chaperone protein complexes can be recovered from bacteria-infected cells including, but not limited to, cells infected with bacteria causing tuberculosis, gonorrhea, typhoid, meningitis, osteomyelitis, meningococcal septicemia, endometritis, conjunctivitis, peritonitis, pyelonephritis, pharyngitis, septic arthritis, Celluloids, epiglottitis, salpingitis, otitis media, shigella dysentery, gastroenteritis, etc. In preferred embodiments, the chaperone proteins or chaperone protein complexes may also be recovered from cells infected with intracellular bacteria, including, but not limited to, Mycobacteria, Rickettsia, Mycoplasma, Neisseria, and Legionella.

In addition, antigenic chaperone protein complexes can also be recovered from cells infected with intracellular protozoa, including, but not limited to, Leishmania, Kokzidioa, and Trypanosoma. Furthermore, chaperone protein complexes can be recovered from cells infected with intracellular parasites including, but not limited to, Chlamydia and Rickettsia. Also encompassed by the invention are the use of cell lines infected with bacteria for recovery of chaperone proteins or chaperone protein complexes.

In another embodiment of the invention, any tissues, or cells isolated from a cancer, including cancer that has metastasized to multiple sites, can be used as a source of chaperone proteins or chaperone protein complexes in the present method. For example, solid tumor tissue (e.g., primary tissue from a biopsy) can be used, leukemic cells circulating in blood, lymph or other body fluids can also be used.

Using the methods of the invention, chaperone proteins or chaperone protein complexes may be recovered from tumor cells, including, but not limited to, for example, tumors that are mesenchymal in origin (sarcomas) i.e., cancers of the following types: fibrosarcomas; myxosarcomas; liposarcomas; chondrosarcomas; osteogenic sarcomas; angiosarcomas; endotheliosarcomas; lymphangiosarcomas; synoviosarcomas; mesotheliosarcomas; Ewing's tumors; myelogenous leukemias; monocytic leukemias; malignant lymphomas; lymphocytic leukemias; plasmacytomas; leiomyosarcomas, and rhabdomyosarcoma. In addition, it is contemplated that this method can be used in the recovery of chaperone proteins or chaperone proteins complexes from tumor cells from tumors that are epithelial in origin (carcinomas) i.e., cancers of the following types: squamous cell or epidermal carcinomas; basal cell carcinomas; sweat gland carcinomas; sebaceous gland carcinomas; adenocarcinomas; papillary carcinomas; papillary adenocarcinomas; cystadenocarcinomas; medullary carcinomas; undifferentiated carcinomas (simplex carcinomas); bronchogenic carcinomas; bronchial carcinomas; melanocarcinomas; renal cell carcinomas; hepatocellular carcinomas; bile duct carcinomas; papillary carcinomas; transitional cell carcinomas; squamous cell carcinomas; choriocarcinomas; seminomas; embryonal carcinomas malignant teratomas; and teratocarcinomas. Chaperone proteins or chaperone protein complexes can also be recovered from cells of leukemia, e.g., cancers of the following types: acute lymphocytic leukemia and acute myelocytic leukemia (myeloblastic, Promyelocytic, myelomonocytic, monocytic, and erythroleukemia); chronic leukemia, e.g., cancers of the following types: (chronic myelocytic (granulocytic) leukemia and chronic lymphocytic leukemia); and polycythemia vera, lymphoma of types: (Hodgkin's disease and non-Hodgkin's disease), multiple mycloma, Waldenström's macroglobulinemia, and heavy chain disease. It is also contemplated that chaperone proteins or chaperone protein complexes may be recovered from tumor cells from tumors induced by chemical carcinogens or radiation. Chemical carcinogens include carcinogens associated with cigarette smoking, such as hydrocarbons and carcinogenic air, food, cosmetics or other pollutants. In another embodiment of the invention, the chaperone proteins or chaperone protein complexes may be recovered from tumor cell lines.

5.2.2. Formulation, Administration and Dosage

Antigenic chaperone protein complexes including aggregated complexes recovered by the methods of the invention can be used to treat or prevent a variety of diseases in animals and humans. The antigenic or immunogenic chaperone protein complexes are capable of eliciting an immune response against the antigenic or immunogenic peptides with which the chaperone proteins are associated. Such immunogenic or antigenic chaperone proteins complexes are useful for the treatment and prevention of cancer and infectious diseases. Chaperone proteins and/or chaperone protein complexes including aggregated complexes are formulated for administration to a subject in need of such treatment or prevention by techniques known in the art.

The present invention relates to a pharmaceutical composition comprised of an effective amount of a chaperone proteins, chaperone protein complexes or aggregates thereof. Said compositions can be administered with a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

Dosages of chaperone protein complexes can be in the range of 1–1,000 micrograms. Preferably the dosage range is 25–500 micrograms. Most preferably the dose range is 1–50 micrograms.

The present invention relates to a vaccine composition comprised of an effective amount of a chaperone proteins, chaperone protein complexes or aggregates thereof. In a specific embodiment, a single dose of vaccine is used, or alternatively an initial vaccination is followed by 1, 2, 3, 4, 5, or more boosters.

Antigenic or immunogenic chaperone protein complexes recovered by the methods of the invention can be used in treatment of cancer and infectious diseases, or in eliciting an immune response. Moreover, therapeutic regimens and pharmaceutical compositions of the invention can be used with additional immune response enhancers or biological response modifiers including, but not limited to, interferon (IFN)-$\alpha$, IFN-$\beta$, IFN-$\gamma$, interleukin (IL)-1, IL-2, IL-4, IL-5, IL-6, IL-12, IL-15, GM-CSF or tumor necrosis factor (TNF)-$\alpha$. The immune response enhancers or biological response modifiers can be provided as proteins or nucleic acids encoding the proteins for the appropriate immune response enhancer or biological response modifiers in combination with the chaperone protein complexes recovered by the methods of the invention (see, for example, U.S. Pat. Nos. 6,147,055, 6,010,849, 5,910,488, 5,641,665).

Formulations for administration via a route such as, but not limited to oral, parenteral, intravenous, intraperitoneal, mucosal, or intradermal, for inhalation, nasal drops, topical gels, and slow release formulations, and preferred dosages thereof are provided for the treatment and prevention of cancer, such as primary and metastatic neoplastic diseases (see U.S. Pat. Nos. 5,948,646, 5,935,576, 5,837,251, 6,017,540, and 6,017,544), the treatment and prevention of infectious diseases (see U.S. Pat. Nos. 5,961,979 and 6,048,530), and adoptive immunotherapy (see U.S. Pat. Nos. 5,985,270 and 5,830,464).

6. EXAMPLES

The following are examples which demonstrate that FS-IEF enriches samples containing chaperone protein complexes for use as a vaccine formulation to treat or prevent cancer. It is also shown that FS-IEF fractions enriched for chaperone proteins contain chaperone proteins that exist in multimeric forms. Specific utility of the enriched fractions as an effective vaccine against the A20 and 12B1 tumors in mice is demonstrated.

6.1. Enrichment of Chaperone Proteins by FS-IEF

FS-IEF was performed on tumor samples from mice. Enriched fractions containing chaperone protein complexes isolated from mouse tumors were found to protect mice that were subsequently challenged with the same tumor. Analysis of fractions enriched in chaperone protein complexes by size exclusion chromatography indicated fractions consisted of high molecular weight species comprised of various chaperone proteins or chaperone protein complexes.

6.1.1. Methods and Materials
Tumor Generation

All tissue/cell culture reagents were purchased from Gibco/BRL (Gaithersburg, Md., USA). A20 murine leukemia/lymphoma cells were cultured at 37° C. and 5% $CO_2$ in RPMI media containing 10% heat inactivated fetal calf serum and supplemented with 2 mM glutamine, 100 U/ml penicillin, 100 mg/ml streptomycin sulfate, 0.025 mg/ml amphotericin B, 0.5×MEM non-essential amino acids, 1 mM sodium pyruvate, and 50 mM 2-mercaptoethanol. Cells were prepared for injection by washing and resuspending them in Hanks' Balanced Salt Solution. The cells were then counted and brought to a concentration of 5×10$^6$ cells/ml. Eight to twelve week old female BALB/c (H-2d) mice (Jackson Laboratories, Bar Harbor, Me., USA) were injected with 0.2 ml (10$^6$ cells) subcutaneously (s.c.) in both flanks and were monitored for tumor development. Tumors greater than 1 cm in diameter were surgically harvested after euthanizing the mice. In vivo passaging of tumors involved harvesting and mincing of the tumor to produce a cell suspension. The cell suspension was spun through a nitex filter to remove debris, and the cell pellet was resuspended, washed, counted, and injected as described above. Mice were housed in a dedicated facility and all animal experimentation was conducted under protocols approved by the University of Arizona Institutional Animal Care and Use Committee. "Principles of laboratory animal care" (NIH publication No. 85–23, revised 1985) were followed accordingly.

Free-Solution Isoelectric Focusing (FS-IEF) for Chaperone Enrichment

In vivo-grown tumor tissue was homogenized at 40° C. using a motor-driven glass-Teflon homogenizer; the buffer was 10 mM Tris-Cl (pH 7.4)/10 mM NaCl, 0.1% octylphenol ethylene oxide condensate/0.1% octylphenoxypoly (ethyleneoxy) ethanol/0.1% tert-octylphenoxy poly (oxyethylene)ethanol (equivalent to Nonidet P-40), with the following protease inhibitors (Roche Molecular Biochemicals, Indianapolis, Ind., USA): leupeptin (2 mg/ml), pepstatin A (1 mg/ml), phenylmethylsulfonyl fluoride (PMSF, 0.5 mM) and a "Complete" protease inhibitor cocktail tablet. This buffer was chosen for its low ionic strength and ability to solubilize membranes. The homogenate was centrifuged at 10,000×g for 30 min at 4° C., and the supernatant was collected. The "low speed" supernatant was centrifuged at 100,000×g for 90 min at 4° C. to obtain a "high speed" supernatant. This supernatant was dialyzed against 5 mM Tris-Cl (pH 7.4)/5 mM NaCl, 0.05% octylphenol ethylene oxide condensate/0.05% octylphenoxypoly (ethyleneoxy) ethanol/0.05% tert-octylphenoxy poly (oxyethylene)ethanol. The dialysate was apportioned and frozen into 5 ml aliquots. One aliquot (approximately 40–50 mg protein) was filtered through a 0.8 $\mu$m filter and readied for isoelectric focusing by adding urea to 6 M, the detergents octylphenol ethylene oxide condensate, octylphenoxypoly (ethyleneoxy) ethanol, and tert-octylphenoxy poly (oxyethylene)ethanol to 0.5% each, ampholytes (2 parts pH 5–8, 1 part pH 3–10; Sigma, St. Louis, Mo., USA) to 5%, and water to a total volume of 60 ml. The high concentrations of detergents and ampholytes were necessary to maintain protein solubility during isoelectric focusing, as proteins often tend to precipitate at or near their pIs. FS-IEF was carried out in a ROTOFOR® device (Bio Rad Laboratories, Hercules, Calif., USA). Isoelectrofocusing was conducted for 4 hrs at 15 W constant power while cooling with recirculating 4° C. water; the anode compartment contained 0.1 M $H_3PO_4$, while the cathode compartment contained 0.1 M NaOH. Twenty fractions were harvested; the pH of each fraction was determined with a standard pH meter, and protein content was analyzed by SDS-PAGE and Western blotting. Following SDS-PAGE proteins were electrotransferred to nitrocellulose and probed with the following primary antibodies specific for each of the chaperone proteins: grp94-spa850; hsp90-spa830; hsp70-spa820; CRT-spa600 (StressGen Biotechnologies, Victoria, British Columbia, Canada). Secondary antibodies were conjugated with alkaline phosphatase (Chemicon International, Temecula, Calif.) Immunoreactive signals were detected by color deposition of the alkaline phosphatase substrate nitroblue tetrazolium/ 5-bromo-4-chloro-3-indolyl phosphate (Boehringer Mannheim, Indianapolis, Ind.) Purification of A20-derived HSP70 was done via conventional and nucleotide affinity chromatography.

Size Exclusion Chromatography (SEC) of FS-IEF Fractions

Chaperone-rich FS-IEF fractions were chosen and pooled, and a 100 µl sample was taken for SEC. SEC was performed on a Waters Alliance 2690 separations module equipped with a PDA 996 photodiode array detector (Waters, Milford, Mass., USA) using a YMC-Pack Diol S5 300 Å column, 6×300 mm (Wilmington, N.C., USA). The column was equilibrated and developed in 6 M urea, 0.4 mM Tris/0.4 mM NaCl, pH 6.0 at a flow rate of 0.5 ml/min. Fractions (1 ml) were collected, and chromatograms were extracted at 214 nm. Size standards (high and low molecular kits, Amersham Pharmacia, Piscataway, N.J., USA) included thyroglobulin (669 kD), ferritin (440 kD), aldolase (158 kD), albumin (67.0 kD), ovalbumin (43.0 kD), chymotrypsinogen A (23.5 kD), and ribonuclease A (13.7 kD). Blue Dextran 2000 (m.w.=2000 kD) was used to determine void volume. Retention times for proteins were converted into elution volumes, which were then used to produce $K_{av}$ values ($K_{av}=V_e-V_o/V_t-V_o$, where $V_t$=total bed volume, $V_o$=void volume, and $V_e$=elution volume of substance of interest). $K_{av}$ values were plotted against log molecular weight of standards to generate a standard curve. Molecular weight determinations of chromatographic peaks in the FS-IEF sample were obtained from the equation of the standard curve. Collected fractions were concentrated with Centricon 10 devices and analyzed for chaperone content via SDS-PAGE and Western blotting as described above. The FS-IEF pooled fractions were also dialyzed into 0.1 M phosphate/0.2 M NaCl, pH 7.0, and chromatographed over the column in the same buffer. Additional controls included chromatography of ampholytes (pH 3–10) under identical conditions as were used for proteins.

Preparation of Chaperone-Enriched Vaccines and in vivo Immunoprotection Experiments Fractions from FS-IEF that contained substantial amounts of four chaperone proteins (HSP70, HSP90, GRP94/gp96, and calreticulin) as determined by SDS-PAGE and Western blotting were dialyzed stepwise out of urea and detergents (starting in 0.1×PBS, 4 M urea, and 0.25% detergents, ending with 0.1×PBS). Fractions were then concentrated by vacuum centrifugation and reconstituted in PBS. Protein concentrations were determined by the BCA method (Pierce, Rockford, Ill., USA, using BSA as a standard), and each concentrated fraction was diluted to 20–200 µg/200 µl in sterile PBS. A20-derived HSP70 was concentrated and prepared for vaccine use in the same fashion.

BALB/c mice were immunized subcutaneously on the flank with 20 µg–200 µg of chosen fractions in 200 ml sterile PBS on days −14 and −7, followed by intravenous (i.v.) challenge with $10^4$ or $10^6$ viable, in vivo-grown A20 leukemia cells on day 0. For dosage escalation studies, 20, 50, 75, 100, or 200 µg of FS-IEF fractions per 200 µl were used for vaccination. Control vaccines consisted of PBS, of A20 tumor lysate, of A20-derived HSP70, or of A20-derived FS-IEF fractions that contained none of the chaperones of interest (as determined by Western blotting). Survival was thereafter monitored; for statistical analyses, the Kaplan-Meier product-limit was used to assess survival. The log-rank statistic was used to test differences between treatment groups.

6.1.2. Enrichment of Chaperone Protein Complexes by FS-IEF Results

Fractions collected from the FS-IEF apparatus were analyzed by SDS-PAGE and stained with Coomassie Blue (FIG. 1a). Most of the proteins from the A20 tumor were found in the pH range of 5.4–6.4. The chaperone protein content of each fraction was determined by Western Blot (FIG. 1b).

Free solution-isoelectric focusing (FS-IEF) yields fractions that are enriched in multiple chaperone proteins.

The separation conditions chosen included nonionic detergents and 6 M urea as a mild chaotropic agent to reduce protein precipitation. Using a Bio Rad ROTOFOR® device, proteins were separated into 20 fractions covering a pH gradient as determined by ampholyte choice. The isoelectric points (pIs) as determined by two-dimensional gel electrophoresis for the murine chaperone proteins from various tissues are as follows: calreticulin (CRT), pH 4.41–4.52; HSP70, pH 5.25–5.30; HSP90, 4.99–5.04; and GRP94/ gp96, 4.86–4.91 (Sanchez, et al., 2000; Swiss-2D PAGE database). These pIs are sufficiently distinct as to allow for adequate separation of each of these proteins via isoelectric focusing. However, SDS-PAGE (FIG. 1, top) and Western blot (FIG. 1, bottom) results indicated that following FS-IEF, several fractions ranging from pH 5.4 to pH 6.4 (lanes 4–11) contained all four of the aforementioned chaperone proteins.

Other chaperone protein members found in those fractions (as indicated by Western blotting with specific antibodies) include the ER HSP70 paralog BiP/GRP78, GRP75/mt HSP70 (mitochondrial HSP70), small amounts of HSP72 (the murine stress-inducible form of HSP70), HSP60, and HSP40, in addition to other unidentified proteins. The FS-IEF enriched chaperone protein complexes or aggregates thereof did not migrate to their predicted or published isoelectric points. Altering the ampholyte ratios during FS-IEF did not enhance separations, and only served to move the overall protein pattern up or down the pH gradient. The nature of this enrichment implied that the chaperone proteins and cohorts were separating as aggregates or multimeric forms rather than with characteristics of individual proteins.

6.1.3. Analysis of the Multiple Chaperone Proteins Results

The multiple chaperone proteins found in FS-IEF fractions are associated in complexes.

Fractions collected from FS-IEF were analyzed by size exclusion chromatography to determine if the chaperone proteins obtained were protein multimers or monomers (FIG. 2). The results indicated that the enriched fractions contained chaperone proteins and complexes thereof that eluted as high molecular weight species. This indicated that the chaperone proteins were multimeric or aggregates (FIG. 2).

If the chaperone proteins were indeed separating as complexes during FS-IEF, rather than as individual proteins, the differences in size between chaperone proteins in the complex and individual chaperone proteins should be evident if molecular sieving techniques are applied. We therefore performed SEC on A20-derived FS-IEF samples that had been enriched for chaperone proteins. The column was run in essentially the same buffer as was used for FS-IEF. As shown in the chromatogram in FIG. 2, approximately 50% of the protein/peptide content in the FS-IEF samples eluted with retention times ($^tR$) between 7 min and 13 min. The bulk of that material eluted with $t_R$ values less than 10, with a peak at approximately 8 min. This peak corresponded to molecular masses above 300 kDa, with shoulder fractions of over 500 kDa, as determined by generating $K_{av}$ values for those peaks and comparing these values with those of standards of known size (see inset, FIG. 2). The standards are denoted by arrowheads placed at their approximate $t_R$ in the chromatogram. It is worth noting that the elution volume of the initial peaks approached that of the void volume ($V_o$, indicated by the blue dextran arrowhead; $t_R \approx 7$ min). Such molecular masses are clearly severalfold larger than those of any single chaperone protein represented here. While the exact composition of the complexes remains unknown, Western blot analyses showed that all four of the immunogenic chaperones (calreticulin, hsp70, hsp90, and grp94/gp96) were present in the SEC fractions under the very high-molecular-mass peak (fractions 1 and 2, FIG. 2, bottom). Carrier ampholytes which are structurally similar to amino acids, almost exclusively contributed to the late eluting, large peak ($t_R > 14$ min, data not shown). Following dialysis of the FS-IEF pooled sample into 0.1 M phosphate/0.2 M NaCl, pH 7.0-, SEC of that sample, performed in that buffer, resulted in peaks of very similar $t_R$. Thus, even in a relatively dissociating buffer such as 6 M urea, the immunogenic chaperones apparently maintained their associations in high-molecular-mass complexes.

6.1.4. Immunization of Mice with FS-IEF Enriched Chaperone Proteins

The chaperone complexes from tumor-derived FS-IEF fractions provided protective immunity when used as prophylactic vaccines.

FS-IEF Compared to A20 Lysate

Figure 3:
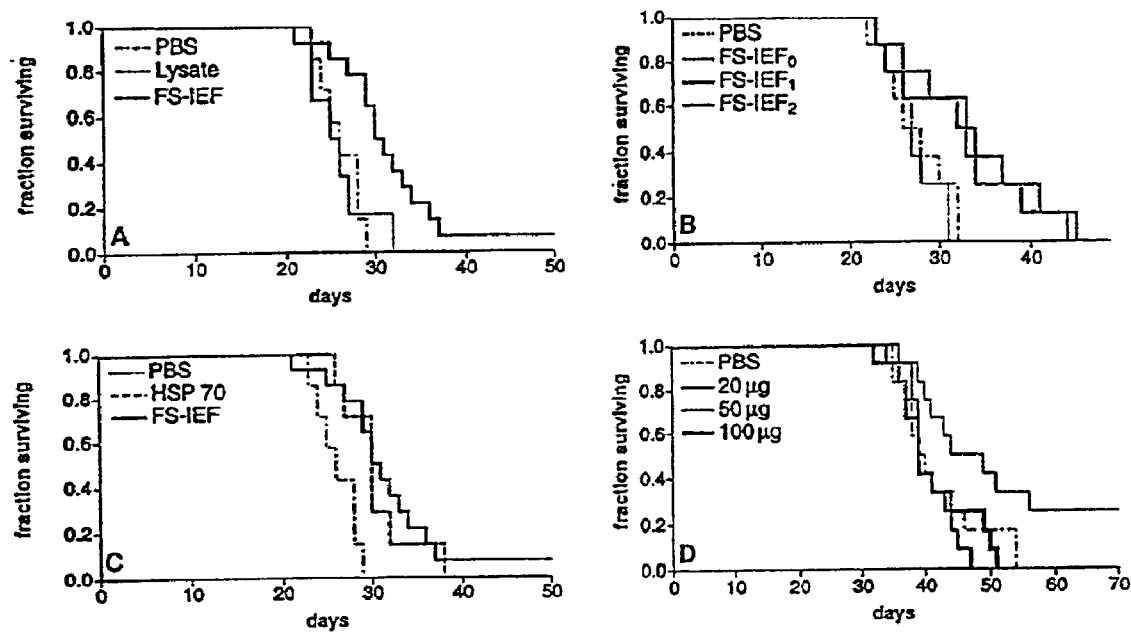

Following FS-IEF of A20 tumor lysate, we identified fractions of interest by SDS-PAGE and Western blotting. The fractions selected were those that contained all four of the previously described immunogenic chaperones grp94 gp96, hsp90, hsp70, and calreticulin. These samples were desalted, concentrated, and injected s.c. into mice as vaccines on days 14 and 7. Viable A20 cells grown in vivo were then given i.v. on day 0, and survival was monitored thereafter. Analysis of survival curves showed that FS-IEF vaccination resulted in statistically significantly longer survival than did mock-vaccinated (PBS) controls (FIG. 3A). In addition, immunization of animals with A20 lystate generated no protection. These data are important since they indicate that unfractionated A20 lysate itself was not a suitable immunogen, and that the FS-IEF steps employed were necessary to enhance the immunogenicity.

Individual FS-IEF Fractions Compared to Each Other

The survival curves shown in FIG. 3A were generated following vaccination of mice with pooled FS-IEF fractions that contained the appropriate chaperones. By breaking down the pool into its individual members, one may determine whether any particular fraction is especially immunodominant. We chose two fractions distinct in overall protein profile but still containing all four of the known immunogenic chaperones (e.g., fractions 4 and 10 from FIG. 1) to be used as vaccines in side-by-side comparisons. As shown in FIG. 3B, vaccination with tumor-derived FS-IEF fractions, designated FS-IEF$_1$ and FS-IEF$_2$, caused mice to survive significantly longer than PBS-treated controls. The FS-IEF$_1$ and FS-IEF$_2$ curves are essentially identical, and are similar to results obtained in mice vaccinated with FS-IEF pooled fractions. It is important to note that irrelevant FS-IEF fractions (i.e., containing little or no detectable chaperone protein, curve FS-IEF$_o$) provided no protective benefit. Thus, no particular FS-IEF fractions contributing to the vaccine pool were immunodominant, and these results were not an artifact of the isofocusing procedure.

FS-IEF Compared to A20-Derived hsp 70

We have previously shown that purified, A20-derived hsp70 was the single most effective immunogen of the four individual chaperone proteins used in these experiments with A20 murine leukemia (Graner et al. 2000, Clin. Can. Res.6:909). In a direct comparison, survival of mice vaccinated with pure A20-derived hsp70 was comparable to that of mice vaccinated with an A20-derived FS-IEF fraction (FIG. 3C). Equal total amounts of protein were used for these vaccinations (20 μg for each of two vaccinations). There was clearly more hsp70 in the single-protein vaccine, because hsp70 made up aminor portion of the 20 μg of the multiprotein vaccine (5%–10%, data not shown). The comparable survival data from the two types of vaccines implied that there was a synergistic effect when multiple chaperone proteins were present in the vaccine.

FS-IEF Dosage Escalation

All of the experiments described above involved vaccination of animals with two 20-μg FS-IEF fractions, hsp70, or A20 tumor lysate. These quantities were based on a dosage of tumor-derived hsp70 found to be effective in generating protective immunity against A20 tumor challenges (Graner et al. 2000, Clin. Can. Res.6:909). Dosage escalation studies were initiated using 20, 50, 75, 100, and 200 μg FS-IEF vaccines. Mice in each dosage group received two vaccinations of the particular assigned dosage (i.e., 20, 50, 75 μg, etc.) on days 14 and 7, followed by i.v. tumor challenge on day 0. Survival curves shown in FIG. 3D demonstrated that dosages in excess of 20 μg actually abrogated immune protection in the face of tumor challenge (for clarity, data dare shown only for dosages of 20, 50, and 100 μg; nearly identical results were obtained for 75-μg and 200-μg injections). Dosages of 50 μg or more are statistically equivalent to saline only. While the nature of this loss of immune protection is not clear, it is obvious that "more is not better" in the case of the vaccine produced by FS-IEF.

6.1.5. Discussion

We have demonstrated that vaccination of mice with A20-leukemia-derived multiple chaperone proteins, prepared by an isoelectric focusing technique (FS-IEF), provided statistically significant immunological protection against an autologous leukemia challenge. This immunoprotective effect was at least equivalent to that provided by A20-derived hsp70, despite the relative paucity of hsp70 in the multichaperone vaccine. The various chaperone-rich FS-IEF fractions were independently capable of providing equivalent protection, but fractions that contained no chaperone proteins or unfractionated A20 tumor lysate failed to provide any protective immunity. Curiously, increasing the vaccine dosage actually nullified the original protective effect. Concerning the physical nature of the chaperone proteins, they do not separate strictly according to published isoelectric points during FS-IEF, and their mobility on size-exclusion chromatography indicates that the proteins are migrating as complexes.

While vaccination against tumor challenge with multiple tumor-derived chaperone proteins has been a goal of ours, we were never able to obtain sufficient quantities of the chaperones by conventional chromatographic methods. Using FS-IEF to produce chaperone-enriched fractions has enabled us to overcome this lack of material. Starting from as little as 1–2 g tumor tissue, we have been able to obtain milligram quantities of enriched chaperone proteins; the potential clinical utility of this is obvious. In addition, the procedure is rapid and relatively uncomplicated, allowing one to generate a vaccine from tumor in 1 day.

The immune response generated following vaccination with tumor-derived FS-IEF samples is due, in part, to an extended multivalency of antigenic peptides escorted by the various chaperone proteins enriched by FS-IEF. Since different chaperone protein family members preferentially escort different peptides, those preferences are exploited by harvesting all of the chaperones of interest, as opposed to enriching for one chaperone at the expense of the others. The results are an expanded antigenic repertoire. At the level of the antigen-presenting cells, having multiple chaperone proteins present in the vaccine will lead to the occupancy of multiple putative chaperone protein receptors on the surfaces of antigen-presenting cells (Binder et al., 2000, Nature Imm. 2:151; Arnold-Schild et al.,1999, J. Exp. Med. 162:3757; Wassenberg et al., 1999, J. Cell Sci. 112:2167). In addition, there are reports of cytokine-releasing effects of chaperone proteins on antigen-presenting cells (Basu et al., 2000, Int. Immun. 12:1531; Todryk et al., 1999, J. Immun. 163: 1398); thus, having multiple chaperones present will result in a greater stimulus for these cells.

Their separation during isoelectric focusing and their mobility during SEC indicate that the tumor-derived, FS-IEF-enriched chaperone proteins are acting in complexes. This results from a "native-state" preservation of chaperone interactions with FS-IEF. These chaperone complexes act as "danger signals" (Matzinger et al., 1994, Annu. Rev. Immunol. 12:991; Melcher et al., 1998, Nat. Med. 4:581; Todryk et al., 1999, J. Immun. 163: 1398; Forsdyke et al., 1999, Cell Stress Chaperones 4:205) for the immune system in ways that individual purified proteins cannot. Dying cells, whether necrotic or apoptotic, do not release individual, purified chaperone proteins during their demise; rather, cellular contents are spilled en masse during necrosis or partitioned into apoptotic bodies during apoptosis. Thus, chaperones in a complex more accurately re-create the danger signal to which the antigen-presenting cells of the immune system are primed to respond.

In the aforementioned scenario, however, the tumor cell lysate is the most appropriate mimic, since it, too, has all of the chaperones and cohorts together. Unlike FS-IEF fractions, however, A20 tumor lysate provided no protective benefit in tumor-rejection experiments. This lack of protective immunity is due to an insufficient concentration of chaperone proteins in the lysate, or to the presence of "tumor-enhancing activities" (Srivastava et al., 1986, Proc. Natl. Acad. Sci. USA 83:3407), or of immune inhibitory substances found in lysate that are removed during FS-IEF. On the other hand, increasing dosages of FS-IEF vaccines over the level of 20 μg/injection led to abrogation of the protective effect of the vaccines. Thus, it would appear that tumor-promoting or immune-inhibiting factors are present in the FS-IEF fractions, but they are at sub-threshold levels in our typical vaccination scheme. These factors are removed during FS-IEF (but are at full strength in the tumor lysate) and reach "effective" levels when larger quantities of FS-IEF vaccines are used. In addition, injection of large quantities of the tumor-derived chaperone grp94 gp96 has been shown to down-regulate the antitumor response usually associated with vaccination by that protein (Chandawarkar et al.,1999, J. Exp. Med. 189:1437). Such an effect, either from grp94 gp96 or from other proteins in the vaccine, is the reason for the loss of immune response with high-dose FS-IEF vaccinations. An additional mechanism for the loss of immune response is the induction of tolerance or of anergy following vaccinations with FS-IEF-derived proteins beyond the optimum, resulting from a hyperabundance of antigen in the vaccines.

In prior work (Graner et al. 2000, Clin. Can. Res.6:909) we found that A20-derived, purified hsp70 was the best immunogen of the four chaperones in the A20 leukemia model. We have shown here that equal amounts of total protein (20 μg) of FS-IEF vaccine and purified, tumor-derived hsp70 are equally immunoprotective. The earlier report (Graner et al. 2000, Clin. Can. Res.6:909) stated that other individual, purified chaperone proteins (grp94/gp96, hsp90, calreticulin) did not protect animals as well as hsp70; thus, it does not seem inherently obvious that adding all four of the chaperone proteins together (in greatly reduced quantities) would improve the vaccine's effectiveness. However, that is the case for FS-IEF vaccines, since they contain all four of the known immunogenic chaperones in smaller amounts than the overall 20-μg quantity of the protein. From the perspective of those four chaperones, the whole is greater than the sum of its parts. The inclusion of co-chaperones and other important proteins also contributes to the apparent synergism between the chaperones.

In previous work (Graner et al. 2000, Clin. Can. Res.6:909) we have mentioned that A20-derived hsp70 vaccination prolongs survival in mice following tumor challenge, an effect equivalent to a 100-fold reduction in tumor burden. FS-IEF-generated vaccines provide at least this level of protection, as well. In light of the aggressive nature of the A20 leukemia and its metastatic potential once introduced into the bloodstream, such protection is substantial for this particular tumor model.

In conclusion, we have developed a technique that provides for the enrichment of chaperone proteins from clarified cell lysates. If the chaperone proteins are derived from tumor tissue, those chaperone-enriched fractions can be used as vaccines that are capable of providing protective immunity to animals that are subsequently challenged from that same tumor type. The procedure is relatively simple, rapid, and efficient, and takes advantage of the increasingly well-documented use of tumor-derived chaperone proteins as agents of antitumor immune responses.

7. Therapeutic Application of FS-IEF Enriched Chaperone Protein Complexes

It was found that FS-IEF fractions enriched in chaperone protein complexes provided therapeutic benefit to mice with pre-existing tumors. Therapeutic benefit against both the A20 and 12B1 tumors was observed.

7.1. Methods and Materials

The ROTORFOR® device (Bio Rad Laboratories, Hercules, Calif.) is attached to a ceramic cooling means that recirculates water maintained at 4° C. in order to prevent heat from accumulating in the device which could denature the proteins. The outlet ports of the ROTORFOR® device (Bio Rad Laboratories, Hercules, Calif.) are covered with tape. An acidic buffer is applied to the anode compartment and a basic buffer is applied to the cathode compartment. The sample is applied to the sample chamber and electrophoresis is conducted at an appropriate power level for an appropriate length of time. As a non-limiting example electrophoresis can be conducted for 5 hours at 15 watts. Also encompassed within the invention is performing FS-IEF using any device known in the art. By way of example, but not as a limitation, an FS-IEF apparatus by Pharmacia (Pharmacia, Peapack, N.J.) can be used.

A mixture of ROTOLYTE®(Bio Rad Laboratories, Hercules, Calif.) buffers was prepared by stirring 5 mls of each buffer in an Erlenmeyer flask. The buffers consisted of the following ROTOLYTES® (Bio Rad Laboratories, Hercules, Calif.): pH 3.9–4.6 A and B; pH 4.1–6.5 A and B; pH5.4–6.8 A and B. Twenty one point six grams of USP grade urea (6M) (Sigma) was slowly added to the buffers and stirred until the urea has completely dissolved. Once the urea has dissolved, the solution was brought to a concentration of 0.4% for each of the following detergents: octylphenol ethylene oxide condensate, octylphenoxypoly (ethyleneoxy) ethanol, and tert-octylphenoxy poly (oxyethylene)ethanol. The addition of the detergents prevented precipitation of the proteins.

The sample consisted of twenty five mgs of soluble protein. The sample was filtered through a 0.8 $\mu$m filter into an Erlenmeyer flask that contained the dissolved urea, detergent and ROTOLYTES® (Bio Rad Laboratories, Hercules, Calif.). The yield of chaperone proteins and complexes after FS-IEF from a sample of this size was in the range of 0.5–1.0 mgs.

Twenty five mls of fresh acid and base buffers (electrophoresis buffers) were added to the anode and cathode chambers of the device respectively and the ROTORFOR® device (Bio Rad Laboratories, Hercules, Calif.) was turned on such that the chamber for the electrophoresis buffers and the sample compartment began to rotate. As an example, but not as a limitation, the buffers in the anode and cathode compartment could consist of 0.1M $H_3PO_4$, and 0.1M NaOH respectively.

Rotation of the device was stopped and the sample was added to the sample compartment using a 10 ml pipette. The sample was distributed evenly throughout the chamber. Rotation of the chamber was commenced again and the safety power lid was attached. Electrophoresis was performed at constant power of about 15 watts. The voltage and current was adjusted to maintain this level of power. Typically, the voltage is 700 V and the current was 21 mA using the electrophoresis buffer described above. Electrophoresis was performed for about five hours.

After five hours the device was turned off and fractions were collected in 12×75 mm tubes. The tubes were placed in a rack which were then placed in a vacuum box. Harvest needles were placed in each tube. The rotation of the device was stopped. The covers from the outlet ports were removed and the tape covering the ports was punctured with pins contained on the harvester array. The vacuum was then turned on and the fractions were collected. The pH of each fraction was determined and an aliquot of each was analyzed by SDS-PAGE and Western blot. Fractions comprising the desired chaperone proteins or chaperone protein complexes was identified, and pooled if required.

7.2.1. 12B1 Tumor

Balb/c mice were injected subcutaneously with 1000 12B1 cells on day 0. On day 2 some mice were injected with cDNA (100 $\mu$g) encoding either interferon gamma or interferon alpha. On day 4 all mice (except for those mice in the negative control/PBS group) received 20 $\mu$g of FS-IEF enriched 12B1 derived chaperone proteins or chaperone protein complexes. The FS-IEF enriched chaperone proteins were obtained using the ROTORFOR® device (Bio Rad Laboratories, Hercules, Calif.) with a pH gradient established using ROTOLYTES® (Bio Rad Laboratories, Hercules, Calif.). The ROTOLYTE® (Bio Rad Laboratories, Hercules, Calif.) mixture consisted of pH 3.9–4.6 A and B; pH 4.1–6.5 A and B; pH 5.4–6.8 A and B. Electrophoresis was conducted for five hours at 15 watts. Thereafter survival was monitored.

Mice receiving only FS-IEF enriched chaperone proteins, or chaperone protein complexes, 4 days after inoculation with 12B1 tumor cells, survived significantly longer than mice that received the negative control (PBS). Mice that received interferon alpha administered on day 2, along with FS-IEF enriched chaperone proteins or chaperone protein complexes administered 4 days after inoculation with 12B1 tumor cells, attained a survival benefit comparable to mice that received enriched chaperone proteins or chaperone protein complexes alone, 4 days after inoculation with 12B1 tumor cells. Mice that received interferon gamma administered alone 2 days after inoculation with 12B1 tumor cells, died sooner than mice receiving the negative control (PBS) indicating that interferon gamma had severe toxic side effects. Administration of interferon gamma 2 days after inoculation with 12B1 tumor cells followed by administration of FS-IEF enriched chaperone proteins, or chaperone protein complexes, 4 days after inoculation with 12B1 tumor cells, survived longer than mice receiving interferon gamma alone (FIG. 4). This suggested the enriched chaperone proteins, or chaperone protein complexes provided a beneficial effect in the context of interferon gamma administration.

7.2.2. A20 Tumor

Balb/c mice were injected subcutaneously with 500,000 A20 cells on day 0 followed by injection of 20 $\mu$g of FS-IEF enriched A20 derived chaperone proteins, or chaperone protein complexes, on day 6 and day 12 after inoculation with the A20 cells. The FS-IEF enriched chaperone proteins were obtained using the ROTORFOR® device (Bio Rad Laboratories, Hercules, Calif.) with a pH gradient established using ROTOLYTES® (Bio Rad Laboratories, Hercules, Calif.). The FS-IEF enriched chaperone proteins were obtained using the ROTORFOR® device (Bio Rad Laboratories, Hercules, Calif.) with a pH gradient established using ROTOLYTES® (Bio Rad Laboratories, Hercules, Calif.). The ROTOLYTE® (Bio Rad Laboratories, Hercules, Calif.) mixture consisted of pH 3.9–4.6 A and B; pH 4.1–6.5 A and B; pH 5.4–6.8 A and B. Electrophoresis was conducted for five hours at 15 watts. Tumor volume was measured at day 11, day 15, day 21, and day 24 post tumor challenge.

Mice receiving FS-IEF enriched A20 derived chaperone proteins, or chaperone protein complexes, on day 6 and day 12 after inoculation with the A20 cells had significantly smaller tumors than mice treated with a negative control (PBS) (FIG. 5).

We have also demonstrated therapeutic effect (i.e. reduction in tumor volume) by administering FS-IEF enriched chaperone proteins from lysates of SA-1 sarcoma cells, BDL-2 lymphoma cells, B16 melanoma cells, and B16 melanoma cells engineered to recombinantly express ovalbumin.

8. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of enriching chaperone protein complexes from a sample comprising chaperone protein complexes, said method comprising the steps of
   (a) subjecting the sample to free solution isoelectric focusing in the presence of a chaotropic agent; and
   (b) collecting one or more fractions with a pH from pH 4.5 to 6.5 which are enriched in chaperone protein complexes.

2. The method of claim 1, wherein said step of subjecting the sample to free solution isoelectric focusing in the presence of a chaotropic agent comprises
   (i) forming a pH gradient that comprises a pH value in the range from pH 4 to pH 7 in a matrix comprising charged buffer particles; and
   (ii) electrophoresing the sample through the pH gradient in the matrix for a period of time until the chaperone protein complexes cease to migrate within the pH gradient.

3. The method of claim 2, wherein said matrix comprises 6 M urea, 0.5% octylphenol ethylene oxide condensate, 0.5% octylphenoxypoly (ethyleneoxy) ethanol, 0.5% tert-octylphenoxy poly(oxyethylene)ethanol, 5 mM Tris/Cl (pH 7.4), and 5 mM NaCl.

4. A method of making a composition enriched with chaperone protein complexes from a plurality of cells, said method comprising the steps of:
   (a) making a cell lysate by lysing the cells with a buffer consisting of 10 mM Tris/Cl, 10 mM NaCl, 0.1% octylphenol ethylene oxide condensate, 0.1% octylphenoxypoly (ethyleneoxy) ethanol, 0.1% tert-octylphenoxy poly(oxyethylene)ethanol 2 µg/ml leupeptin, 1 µg/ml pepstatin A, and 0.5 mM phenylmethylsulfonyl fluoride;
   (b) dialyzing the cell lysate from (a) into a buffer consisting of 5 mM Tris/Cl, 5 mM NaCl, 0.05% octylphenol ethylene oxide condensate, 0.05% octylphenoxypoly (ethyleneoxy) ethanol, 0.05% tert-octylphenoxy poly(oxyethylene)ethanol;
   (c) dialyzing the cell lysate from (b) into a buffer consisting of 2.5 mM Tris/Cl, 2.5 mM NaCl, 0.025% octylphenol ethylene oxide condensate, 0.025% octylphenoxypoly (ethyleneoxy) ethanol, 0.025% (octylphenoxy) polyethoxyethanol;
   (d) dialyzing the cell lysate from (c) into a buffer consisting of 1.25 mM Tris/Cl, 1.25 mM NaCl, 0.012% octylphenol ethylene oxide condensate, 0.012% octylphenoxypoly (ethyleneoxy) ethanol, 0.012% tert-octylphenoxy poly(oxyethylene)ethanol;
   (e) dialyzing the cell lysate from (d) into water;
   (f) adding the cell lysate from (e) to a solution comprising urea and ampholytes;
   (g) forming a pH gradient that comprises a pH value in the range from pH 4 to pH 7 in a buffer comprising 6M urea, 0.4% octylphenol ethylene oxide condensate, 0.4% octylphenoxypoly (ethyleneoxy) ethanol, 0.4% tert-octylphenoxy poly(oxyethylene)ethanol and 30 ml of ampholytes;
   (h) electrophoresing the cell lysate (f) through the pH gradient in the matrix with a voltage of 500 to 2000 volts for 5 hours;
   (i) collecting one or more fractions with a pH from pH 4.5 to 6.5; and
   (j) dialyzing the fractions against a solution comprising phosphate buffered saline.

5. A pharmaceutical composition comprising a sample enriched in chaperone protein complexes, and a pharmaceutically acceptable excipient, wherein the sample is prepared by a method comprising:
   (a) subjecting a solution comprising chaperone protein complexes and a plurality of different proteins to isoelectric focusing in the presence of a chaotropic agent, and
   (b) collecting one or more fractions with a pH from pH4.5 to 6.5; wherein at least some of the proteins in the solution are present in fractions other than fractions of pH 4.5 to pH 6.5; wherein the collected fractions comprise a mixture of chaperone protein complexes;
   (c) wherein said chaperone protein complexes in said sample are not purified to homogeneity.

6. The pharmaceutical composition of claim 5, wherein said sample comprises pooled proteins from said collected fractions.

7. The pharmaceutical composition of claim 5, wherein the chaperone protein complexes are present in aggregates that have a molecular weight that is greater than 300 kD.

8. The pharmaceutical composition of claim 7, wherein the aggregate chaperone protein complexes comprise GRP94/gp96, HSP 90, HSP70, calreticulin, BiP/grp78, grp75/mt, HSP 70, HSP72, HSP60, and HSP40.

9. The method of claim 1, wherein the chaotropic agent is urea.

10. The method of claim 1 or 9, wherein said free solution isoelectric focusing is performed in the presence of detergent.

11. The method of claim 2, wherein said matrix comprises said chaotropic agent and a detergent.

12. The method of claim 10 wherein said detergent is nonionic.

13. The method of claim 11 wherein said detergent is nonionic.

14. The method of claim 3 or 11 wherein said chaotropic agent is urea.

15. The method of claim 14, wherein said chaotropic agent is 6 M urea.

16. The method of claim 12 wherein the nonionic detergent is one or more of octylphenol ethylene oxide condensate, octylphenoxypoly (ethyleneoxy) ethanol, or (octylphenoxy) polyethoxyethanol.

17. The method of 13 wherein the nonionic detergent is one or more of octylphenol ethylene oxide condensate, octylphenoxypoly (ethyleneoxy) ethanol, or (octylphenoxy) polyethoxyethanol.

18. The method of claim 2, wherein said matrix comprises 0.5% octylphenol ethylene oxide condensate, 0.5% octylphenoxypoly (ethyleneoxy) ethanol, and 0.5% (octylphenoxy) polyethoxyethanol.

19. The method of claim 16 or 17, wherein said matrix comprises 0.5% octylphenol ethylene oxide condensate, 0.5% octylphenoxypoly (ethyleneoxy) ethanol, and 0.5% (octylphenoxy) polyethoxyethanol.

20. The pharmaceutical composition of claim 5, wherein said chaotropic agent is urea.

21. The pharmaceutical composition of claim 20, wherein said chaotropic agent is 6 M urea.

22. The pharmaceutical composition of claim 5 or 20, wherein the isoelectric focusing is performed in the presence of detergent.

23. The pharmaceutical composition of claim 22, wherein said detergent is nonionic.

24. The pharmaceutical composition of claim 23, wherein said nonionic detergent is one or more of octylphenol ethylene oxide condensate, octylphenoxypoly (ethyleneoxy) ethanol, or (octylphenoxy) polyethoxyethanol.

25. The pharmaceutical composition of claim 24, wherein said nonionic detergent comprises 0.5% octylphenol ethylene oxide condensate, 0.5% octylphenoxypoly (ethyleneoxy) ethanol, and 0.5% (octylphenoxy) polyethoxyethanol.

26. The pharmaceutical composition of claim 5, wherein the isoelectric focusing is performed in the presence of 6 M urea, 0.5% octylphenol ethylene oxide condensate, 0.5% octylphenoxypoly (ethyleneoxy) ethanol, 0.5% (octylphenoxy) polyethoxyethanol, 5 mM Tris/Cl (pH 7.4), and 5 mM NaCl.

* * * * *